United States Patent
Takeoka et al.

(10) Patent No.: US 9,956,751 B2
(45) Date of Patent: *May 1, 2018

(54) THIN FILM POLYMER STRUCTURE HAVING DIFFERENT MODIFICATION ON OPPOSITE SIDES THEREOF

(71) Applicants: NANOTHETA CO, LTD., Tokyo (JP); TORAY INDUSTRIES, INC., Tokyo (JP); Shinji Takeoka, Tokyo (JP)

(72) Inventors: Shinji Takeoka, Tokyo (JP); Yosuke Okamura, Matsudo (JP); Toshinori Fujie, Nishitokyo (JP); Saori Utsunomiya, Moriya (JP); Takahiro Goto, Shibata (JP)

(73) Assignees: NANOTHETA CO, LTD., Tokyo (JP); TORAY INDUSTRIES, INC., Tokyo (JP); Shinji Takeoka, Tokyo (JP)

(*) Notice: Subject to any disclaimer, the term of this patent is extended or adjusted under 35 U.S.C. 154(b) by 50 days.

This patent is subject to a terminal disclaimer.

(21) Appl. No.: 13/904,882

(22) Filed: May 29, 2013

(65) Prior Publication Data
US 2014/0158287 A1 Jun. 12, 2014

Related U.S. Application Data

(62) Division of application No. 12/312,069, and a division of application No. PCT/JP2007/071437, filed on Oct. 29, 2007.

(30) Foreign Application Priority Data

Oct. 27, 2006 (JP) ................................ 2006-292688

(51) Int. Cl.
*B32B 37/02* (2006.01)
*B32B 27/00* (2006.01)
(Continued)

(52) U.S. Cl.
CPC ............ *B32B 37/02* (2013.01); *A61K 9/7007* (2013.01); *B32B 38/10* (2013.01); *C08J 5/18* (2013.01);
(Continued)

(58) Field of Classification Search
None
See application file for complete search history.

(56) References Cited

U.S. PATENT DOCUMENTS

| | | | |
|---|---|---|---|
| 4,987,032 A | 1/1991 | Miyasaka et al. | |
| 5,071,909 A | 12/1991 | Pappin et al. | |

(Continued)

FOREIGN PATENT DOCUMENTS

| | | |
|---|---|---|
| EP | 0 344 799 A2 | 12/1989 |
| EP | 0511590 A1 | 11/1992 |

(Continued)

OTHER PUBLICATIONS

Chinese Office Action for corresponding Chinese Application No. 201210206346.8 dated Dec. 4, 2013.
(Continued)

*Primary Examiner* — Kevin S Orwig
(74) *Attorney, Agent, or Firm* — Birch, Stewart, Kolasch & Birch, LLP

(57) ABSTRACT

A thin film polymer structure having a functional substance on the face (A surface) and reverse face (B surface) of the film, obtained by the steps of:
  (a) causing polyfunctional molecules to adsorb to an area of an arbitrary shape in an interface between a substrate body and a liquid phase;
  (b) polymerizing and/or crosslinking the adsorbing polyfunctional molecules to form a polymer thin film;
  (c) bonding a functional substance to the A surface of the formed thin film and then (Continued)

(d) forming a soluble support film thereon; exfoliating the thin film and the soluble support film from the substrate body;

(e) bonding to the B surface of the thin film a functional substance identical to or different from the abovementioned functional substance and then dissolving the soluble support film with a solvent.

8 Claims, 24 Drawing Sheets

(51) Int. Cl.
| | | |
|---|---|---|
| A61K 9/70 | (2006.01) | |
| C08J 5/18 | (2006.01) | |
| C08J 7/12 | (2006.01) | |
| C12N 5/00 | (2006.01) | |
| B32B 38/10 | (2006.01) | |
| A61K 9/00 | (2006.01) | |

(52) U.S. Cl.
CPC .............. *C08J 7/12* (2013.01); *C12N 5/0068* (2013.01); *A61K 9/0014* (2013.01); *A61K 9/70* (2013.01); *C12N 2535/10* (2013.01); *Y10T 156/10* (2015.01); *Y10T 428/31504* (2015.04)

(56) References Cited

U.S. PATENT DOCUMENTS

| | | |
|---|---|---|
| 6,020,175 A | 2/2000 | Onda et al. |
| 6,114,099 A | 9/2000 | Liu et al. |
| 6,689,338 B2 | 2/2004 | Kotov |
| 2001/0046564 A1 | 11/2001 | Kotov |
| 2002/0015679 A1 | 2/2002 | Kotov |
| 2004/0038007 A1 | 2/2004 | Kotov et al. |
| 2004/0071909 A1 | 4/2004 | McGlothlin et al. |
| 2004/0112237 A1 | 6/2004 | Chaug et al. |
| 2012/0034466 A1 | 2/2012 | Takeoka et al. |

FOREIGN PATENT DOCUMENTS

| | | |
|---|---|---|
| EP | 1 785 448 A1 | 5/2007 |
| JP | 3-141300 A | 6/1991 |
| JP | 2966795 B2 | 8/1999 |
| JP | 3020428 B2 | 1/2000 |
| JP | 2000-143705 A | 5/2000 |
| JP | 2003-528755 A | 9/2003 |
| JP | 2003-535063 A | 11/2003 |
| WO | WO 01/72878 A1 | 10/2001 |
| WO | WO 01/91808 A2 | 12/2001 |
| WO | WO 02/076428 A1 | 10/2002 |
| WO | WO 03/103854 A1 | 12/2003 |
| WO | WO 2004/058308 A1 | 7/2004 |
| WO | WO 2006/004537 A1 | 1/2006 |
| WO | WO 2006/025592 A1 | 3/2006 |

OTHER PUBLICATIONS

Boulmedais et al., Polyelectrolyte Multilayer Films with Pegylated Polypeptides as a New Type of Anti-Microbial Protection for Biomaterials, Biomaterials, May 2004, pp. 2003-2011, vol. 25.

Chaki et al., Self-Assembled Monolayers as a Tunable Platform for Biosensor Applications, Biosensors and Bioelectronics, Jan. 2002, pp. 1-12, vol. 17.

Domoto et al., Fluoro-resin Thin Film Prodn. using Carrier Film—Involves Coating Filling Resin Dispersion onto Carrier Sheet and Heating, Formed Film Surface is then Treated for Bonding and Avoiding Creasing, Database WPI, Thomson Scientific, AN 1992-162165, XP-002443631, Abstract, Mar. 24, 1992, p. 1.

Extended European Search Report dated Aug. 7, 2007 for European Patent Application No. 05782124.1.

Extended European Search Report dated Sep. 20, 2012, for European Application No. 07831170.1.

Fujieda et al., Construction of Nanosheets Consisting of Sodium Alginate and Chitosan with Hetero Surface, CSJ: The Chemical Society of Japan Koen Yokoshu, Mar. 13, 2006, p. 469, vol. 86, No. 1.

Gittins et al., Tailoring the Polyelectrolyte Coating of Metal Nanoparticles, Journal of Physical Chemistry B, Jun. 27, 2001, pp. 6846-6852, vol. 105, No. 29.

Goto et al., Preparation of Albumin Nano-Sheets using Hydrophobic and Hydrophilic Patterning Substrate, CSJ: The Chemical Society of Japan Koen Yokoshu, Mar. 13, 2006, p. 576, vol. 86, No. 1.

Kurihara et al., "Manufacture of Polymeric Thin Film useful as Carrier for Solid Sensor, involves Immersing Solid Surface into a Liquid . . . Surface", Database WPI, Thomson Scientific, AN 2000-434049, XP-002443632, Abstract, May 26, 2000, p. 1.

Kurihara et al., "Manufacture of Polymeric Thin Film Useful as Carrier for Solid Sensor, Involves Immersing Solid Surface Liquid . . . Surface", Database WPI, Thomson Scientific, AN 2000-434049, XP002683156, Abstract, May 26, 2000, pp. 1-2.

Mallwitz et al., Physically Cross-Linked Ultrathin Elastomeric Membranes, Angew. Chem. Int. Ed., 2001, pp. 2654-2647, vol. 40, No. 14.

Mamedov et al., Free-Standing Layer-by-Layer Assembled Films of Magnetite Nanoparticles, Langmuir, May 27, 2000, pp. 5530-5533, vol. 16, No. 13.

Mamedov et al. Molecular Design of Strong Single-Wall Carbon Nanotube/Polyelectrolyte Multilayer Composites, Nature Materials, Dec. 2002, pp. 109-194, vol. 1.

Marinakos et al., Gold Particles as Templates for the Synthesis of Hollow Polymer Capsules. Control of Capsule Dimensions and Guest Encapsulation, J. Am. Chem. Soc., XP-002443636, 1999, pp. 8518-8522, vol. 121.

Mattsson et al., Quantifying Glass Transition Behavior in Ultrathin Free-Standing Polymer Films, Physical Review E, Oct. 2000, pp. 5187-5200, vol. 62, No. 4.

Nardin et al., Giant Free-Standing ABA Triblock Copolymer Membranes, Langmuir, 2000, pp. 7708-7712, vol. 16, No. 20.

Stroock et al., Synthesis of Free-Standing Quasi-Two-Dimensional Polymers, Langmuir, 2003, pp. 2466-2472, vol. 19, No. 6.

Tang et al., Nanostructured Artificial Nacre, Nature Materials, Jun. 2003, p. 413-418, vol. 2, with one page of Supplementary Information.

U.S. Advisory Action dated Mar. 7, 2013 for U.S. Appl. No. 12/312,069.

U.S. Advisory Action dated May 2, 2013 for U.S. Appl. No. 12/312,069.

U.S. Advisory Action dated Nov. 22, 2010 for U.S. Appl. No. 11/658,908.

U.S. Final Office Action dated Aug. 11, 2010 for U.S. Appl. No. 11/658,908.

U.S. Final Office Action dated Nov. 28, 2012 for U.S. Appl. No. 12/312,069.

U.S. Non-Final Office Action dated Apr. 2, 2010 for U.S. Appl. No. 11/658,908.

U.S. Non-Final Office Action dated May 17, 2012 for U.S. Appl. No. 12/312,069.

Utsunomiya et al., Preparation of Particle-Fused Microsheets using a Hydrophilic/Hydrophobic Patterning Substrate and Hetero-Modification of Both Sides, Abstracts of Symposium on Colloid and Surface Chemistry, Aug. 30, 2006, p. 396, vol. 59.

Wouters et al., Nanolithography and Nanochemistry: Probe-Related Patterning Techniques and Chemical Modification for Nanometer-Sized Devices, Angewandte Chemie International Edition, 2004, pp. 2480-2495, vol. 43.

Wu et al., Synthesis of Nanometer-Sized Hollow Polymer Capsules from Alkanethiol-Coated Gold Particles, Chem. Commun., XP-002443637, 2000, pp. 775-776.

Xu et al., Polymer—Silicon Hybrid Monolayers as Precursors for Ultrathin Free-Standing Porous Membranes, Langmuir, 2002, pp. 2363-2367, vol. 18, No. 6.

(56) References Cited

OTHER PUBLICATIONS

English translation of the International Preliminary Report on Patentability and Written Opinion of the International Searching Authority (Forms PCT/IB/373 and PCT/ISA/237) for International Application No. PCT/JP2005/016371, dated Feb. 28, 2007.

U.S. Office Action for U.S. Appl. No. 12/312,069, dated Jan. 2, 2015.

U.S. Office Action for U.S. Appl. No. 12/312,069, dated May 22, 2015.

U.S. Office Action for U.S. Appl. No. 12/312,069 dated Dec. 2, 2015.

U.S. Office Action for U.S. Appl. No. 12/312,069 dated Mar. 29, 2016.

U.S. Office Action for U.S. Appl. No. 12/312,069, dated Nov. 16, 2016.

THIN FILM POLYMER STRUCTURE HAVING DIFFERENT MODIFICATION ON OPPOSITE SIDES THEREOF

CROSS REFERENCE TO RELATED APPLICATIONS

This application is a Divisional of copending U.S. application Ser. No. 12/312,069 filed on Nov. 10, 2009, which is a National Phase of PCT International Application No. PCT/JP2007/071437 filed on Oct. 29, 2007, which claims priority to Japanese Application No. 2006-292688 filed in Japan, on Oct. 27, 2006. The entire contents of all of the above applications is hereby incorporated by reference.

TECHNICAL FIELD

The present invention relates to a thin film polymer structure having identical or different functional substances on its face (A surface) and reverse face (B surface) and a method for preparing the same.

BACKGROUND OF THE INVENTION

As methods for creating organic molecular thin films, a spin-coating method, an electrolytic polymerization method, a vapor deposition method, a vapor deposition polymerization method and the like are conventionally used. As a method for forming an alignment layer, the Langmuir-Blodgett (LB) method is well known. This method is performed as follows. Amphiphilic molecules are dissolved in a volatile organic solvent to be developed on a gas-liquid interface. After the solvent is vaporized, the resultant substance is compressed. The resultant monomolecular layer is transferred to a solid substrate. With this method, the number of the thin film layers and the order of lamination can be controlled. However, this method is only applicable to molecules which can be developed on a water surface as a monomolecular layer and thus is only effective for amphiphilic molecules, which are water-insoluble. The LB method is not efficient because the equipment to be used is expensive and cannot be easily handled.

A technology has been established for forming a self-assembled monolayer (SAM) including organic molecules regularly and stably aligned on a surface of a metal material such as gold or platinum, or a surface of an inorganic material such as silicon, silica or glass. Features of this technology are that the monolayer is strongly bonded to the substrate and so is stable, and the monolayer can be formed at low cost and in a simple manner without using any special equipment by merely immersing the substrate in a solution. In addition, this technology is applicable to a substrate having a complicated shape. This technology is attracting attention as, for example, a nanotechnology for constructing a pattern of organic molecules on an ultrafine pattern formed by a lithography technology[4].

An attempt is progressing to construct a three-dimensional structure in a bottom-up manner by laminating molecules on a two-dimensional plane by, for example, a layer-by-layer (LbL) method using electrostatic interaction of polyelectrolytes. This lamination method is based on the following principle. A substrate surface is immersed in a polyelectrolyte solution having the opposite charge to that of the substrate surface, so that one layer of the polyelectrolyte adsorbs to the substrate surface by electrostatic interaction. At this point, the substrate surface is newly charged oppositely by the excessive charges of the adsorbing polyelectrolyte. Next, one layer of the polyelectrolyte having the opposite charge to that of the polyelectrolyte layer already adsorbing is caused to adsorb to the surface. By repeating this process, a multi-layer structure controlled to have an arbitrary thickness can be formed. For example, it has been reported that an enzyme is immobilized, by electrostatic interaction, on a structure obtained by the LbL method, for the purpose of developing new molecular devices including enzyme reactors, biosensors and light emitting devices[1,2]. This method allows a three-dimensional structure to be prepared in a simple manner without using any special equipment and so is suitable to immobilize molecules of proteins or the like which may become denatured. In recent years, a method wherein a structure is obtained by forming a structure obtained through an LbL method atop a nonionic sacrificial film and then the sacrificial film is dissolved has been proposed[5]. A technology for forming, atop a SAM, a structure obtained through an LbL method and then transferring the structure to a support film has also been reported[6].

The present inventors previously submitted a thin film polymer structure of arbitrary shape and preparation method therefor[3]. For example, after forming a self-assembled monolayer on a round gold substrate body and subsequently adsorbing and crosslinking albumin thereto, the round albumin polymer thin film is easily caused to exfoliate from the gold substrate body through surfactant processing.

It is known that a hollow structure having a hollow of the shape of the mold can be obtained by forming a polyelectrolyte complex on the surface of a mold formed of an inorganic or metal microparticle or cell and then dissolving the mold[7]. As the microparticle forming the mold, silica, latex bead, melamine resin or the like is used. The mold is dissolved by HF (hydrogen fluoride), an organic solvent, an acid or the like. There is no problem where a spherical microparticle is used as a mold, but a mold having a complicated shape is highly precise and thus is expensive like a printing plate or a plastic mold. Therefore, this method is usable only when the mold is stable and reusable. Since the above-described structures are formed in a bottom-up manner from the substrate, the surface of such a structure in contact with the substrate is not modified even after the structure is freed from the substrate.

There are no reports related to a method for modifying the surface in contact with the substrate for a structure obtained by existing nanotechnology. Also, a method whereby the face and reverse face of a thin film polymer structure in a dispersion state are easily and reliably modified with separate functional molecules is not known.

REFERENCES

1. Japanese Patent No. 3020428
2. Japanese Patent 2966795
3. WO 2006/025592 No. Pamphlet
4. Daan, W et al., Angew. Chem. Int. Ed, 43, 2480-2495 (2004).
5. Mamedov, A. A. et al., Langmuir, 16, 5530-5533 (2000).
6. Stroock, A. D. et al., Langmuir, 19, 2466-2472 (2003).
7. David, I. et al., J. Phys. Chem. B, 105, 6846-6852 (2001).

DISCLOSURE OF THE INVENTION

The present invention has an object of providing a thin film polymer structure having identical or different functional substances on its face (A surface) and reverse face (B surface) and a method for preparing the same.

As a result of active studies conducted in order to solve the above-described problems, the present inventors found that a thin film structure is obtained by forming a rectangularly-patterned, self-assembled monolayer on, for example, a silicon substrate body, then causing albumin as polyfunctional molecules to adsorb thereto and crosslinking albumin, then bonding a functional substance to the face, which is one of the surfaces of the thin film (the front face, called the "A surface"), exfoliating a albumin polymer thin film from the gold substrate body through the use of a soluble support film, bonding an identical or different functional substance to the other surface of the thin film (called the "B surface"), and using a solvent to dissolve the support film. Thus, the present invention has been completed. The present inventors also found the following. A thin film structure is obtained by bonding a functional substance to the A surface of the thin film, exfoliating the thin film from the substrate body by dissolving the soluble support film in solvent, and then applying the surface of the exfoliated thin film atop the soluble support film formed on a substrate body different from the aforementioned substrate body, bonding a functional substance identical to or different from the aforementioned functional substance to the B surface of the thin film, and then dissolving the support film in a solvent. Thus, the present invention has been completed.

Namely, the present invention is directed to the following.

1. A thin film polymer structure having a functional substance on the face (A surface) and reverse face (B surface) of the film.
2. A thin film polymer structure having a functional substance on the A surface and B surface of the film, said polymer structure obtained by the steps of:
   (a) adsorbing polyfunctional molecules to a region of an arbitrary shape in an interface between a substrate body and a liquid phase;
   (b) polymerizing and/or crosslinking the adsorbing polyfunctional molecules to form a polymer thin film;
   (c) bonding a functional substance to the A surface of the formed thin film and then forming a soluble support film thereon;
   (d) exfoliating the thin film and the soluble support film from the substrate body; and
   (e) bonding to the B surface of the thin film a functional substance identical to or different from the functional substance bonded to the A surface and then dissolving the soluble support film with a solvent.
3. A thin film polymer structure having a functional substance on the A surface and B surface of the film, said polymer structure obtained by the steps of:
   (a) adsorbing polyfunctional molecules to a soluble region of an arbitrary shape in an interface between a substrate body and a liquid phase;
   (b) polymerizing and/or crosslinking the adsorbing polyfunctional molecules to form a polymer thin film;
   (c) bonding a functional substance to the A surface of the formed thin film and then;
   (d) exfoliating the thin film from the substrate body by dissolving the soluble region with a solvent;
   (e) applying the A surface of the exfoliated thin film atop the soluble support film formed on a substrate body other than the abovementioned substrate body; and
   (f) bonding a functional substance identical to or different from the aforementioned functional substance to the B surface of the formed thin film and then dissolving the soluble support film with a solvent.
4. A method for preparing a thin film polymer structure having a functional substance on the A surface and B surface of the film, said polymer structure obtained by the steps of:
   (a) adsorbing polyfunctional molecules to a region of an arbitrary shape in an interface between a substrate body and a liquid phase;
   (b) polymerizing and/or crosslinking the adsorbing polyfunctional molecules to form a polymer thin film;
   (c) bonding a functional substance to the A surface of the formed thin film and then forming a soluble support film thereon;
   (d) exfoliating the thin film and the soluble support film from the substrate body; and
   (e) bonding to the B surface of the thin film a functional substance identical to or different from the functional substance bonded to the A surface and then dissolving the soluble support film with a solvent.
5. A method for preparing a thin film polymer structure having a functional substance on the A surface and B surface of the film, said polymer structure obtained by the steps of:
   (a) adsorbing polyfunctional molecules to a soluble region of an arbitrary shape in an interface between a substrate body and a liquid phase;
   (b) polymerizing and/or crosslinking the adsorbing polyfunctional molecules to form a polymer thin film;
   (c) bonding a functional substance to the A surface of the formed thin film and then;
   (d) exfoliating the thin film from the substrate body by dissolving the soluble region with a solvent;
   (e) applying the A surface of the exfoliated thin film atop the soluble support film formed on a substrate body other than the abovementioned substrate body; and
   (f) bonding to the B surface of the thin film a functional substance identical to or different from the abovementioned functional substance, and then dissolving the soluble support film with a solvent.

In the present invention, the step of polymerizing and/or crosslinking the polyfunctional molecules may further comprise the step of laminating polyelectrolytes having opposite charges to each other alternately to crosslink the polyelectrolytes in terms of charges. The polyfunctional molecules may be, for example, of a polyfunctional monomer and/or a polyfunctional macromer. The polyfunctional macromer is, for example, at least one of the following selected from the group consisting of a protein, a polylactic acid, a polylactic acid/glycolic acid copolymer, polycaprolactone, a polyelectrolyte, and a polymer bead. In the present invention, the polyfunctional macromers are crosslinked by, for example, physical crosslinking such as thermal denaturing or thermal plasticity or by fusion.

In the present invention, the functional substance is, for example, at least one of the following selected from the group consisting of a polymer compound, a polyelectrolyte, a protein, a peptide, a polysaccharide, and a biotin derivative.

Further, in the present invention, the region is preferably a self-assembled monolayer or a self-assembled bilayer. Here, the self-assembled monolayer may be formed of linear hydrophobic molecules having at least one of the following groups selected from the group consisting of, at a terminus, an SH group, a chloroalkylsilyl group, an alkoxyalkylsilyl group, and a vinyl group.

In the present invention, the substrate body is entirely or partially formed of a metal or an oxide cover layer thereof, silicon, silicon rubber, silica or glass, mica, a carbon material such as graphite, a polymer material such as polyethylene, polypropylene, cellophane, or an elastomer, or a calcium compound such as apatite.

In the present invention, the soluble support film or soluble region is formed of a polyelectrolyte such as a polyacrylic acid or a polymethacrylic acid, polyethylene glycol, polyacrylamide, polyvinyl alcohol, a nonionic water-soluble polymer such as a polysaccharide such as starch or acetylcellulose, or a resin such as novolac.

Further, in the present invention, the solvent is selected from acetone, acetic ether, an alcohol, water, or an aqueous solution and does not dissolve the thin film polymer structure.

In the present invention, the dispersion formed when the structure is dispersed in liquid may be obtained by dissolving the soluble support film or soluble region in a solvent.

In the present invention, the structure can be a thin film polymer structure adhered to the interface by application, coating, or the like. Examples of an interface include at least one of the following selected from the group consisting of a cell, a tissue, an internal organ, a vascular wall, a mucous membrane, a cornea, skin, hair, or a nail.

The present invention provides a thin film polymer structure having an arbitrary shape with identical or different functional materials on its face and reverse face and a method for preparing the same. The structure of the present invention, when bonded with a target labeling site or the like, can be used as a functional carrier or a platelet substitute in a drug delivery system, a wound coating material, a coagulation inhibitor, or a topical skin product such as a skin care product.

BRIEF DESCRIPTION OF THE DRAWINGS

FIG. 4(a) shows a three-dimensional view; FIG. 4(b) shows a two-dimensional view seen from above; and FIG. 4(c) shows a cross-section pattern diagram.

FIG. 9(a) shows the LbL nanosheet floating in acetone after exfoliation from the substrate; FIG. 9(b) shows the LbL nanosheet in atmosphere after being scooped with a metal frame.

FIG. 10(a) shows a two-dimensional view seen from above; FIG. 10(b) shows a three-dimensional view; and FIG. 10(c) shows a cross-section pattern diagram.

In FIG. 14, the A surface and B surface were modified with latex beads having a particle diameter of 200 nm and 2 μm, respectively.

FIG. 16(a) shows a nanosheet on silicon rubber adhered to skin; FIG. 16(b) shows skin after water has been used to dissolve the support film between silicon rubber and a nanosheet and the silicon rubber has been exfoliated (under visible light); FIG. 16(c) shows the same situation as the picture to its left (under blacklight exposure).

FIG. 18(b) is an enlarged view of FIG. 18(a).

FIG. 23(a) shows the A surface before rHSA adsorption; FIG. 23(b) shows the A surface after rHSA adsorption; and FIG. 23(c) shows the B surface.

BEST MODE FOR CARRYING OUT THE INVENTION

Figure 1:
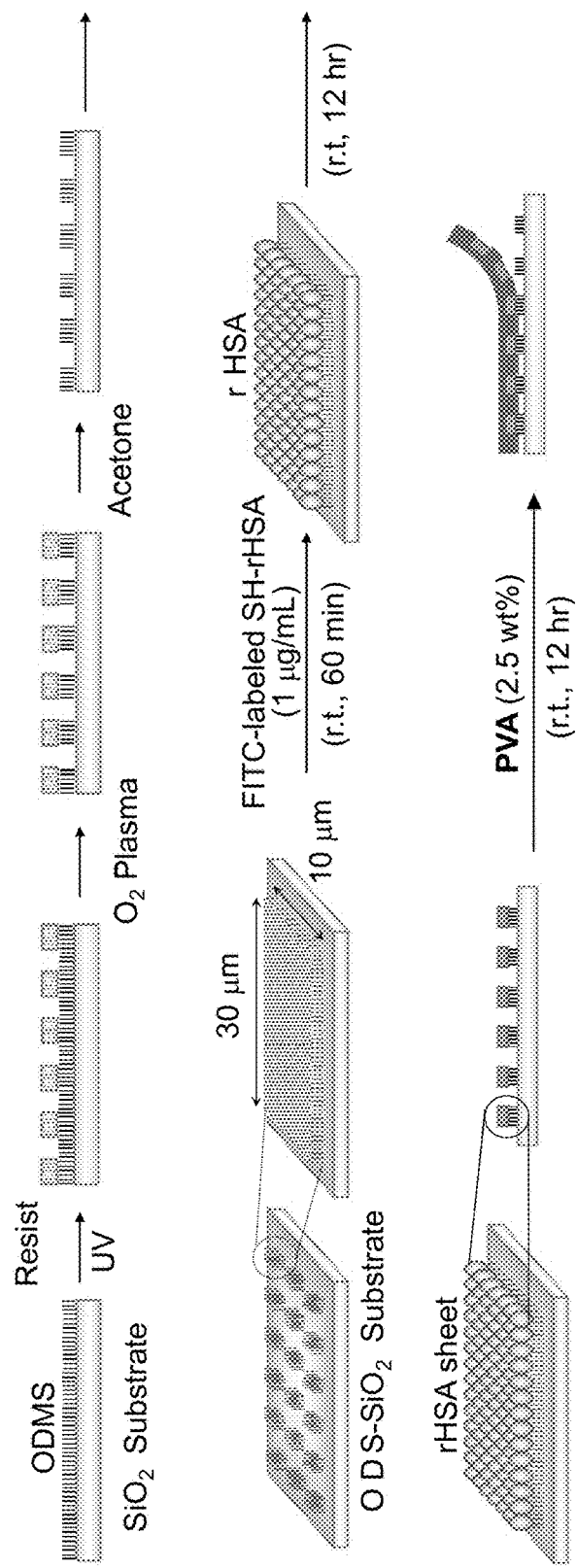
FIG. 1 shows an outline of ODMS-SiO$_2$ substrate production and the HSA adsorption and exfoliation processes.

Hereinafter, embodiments of the present invention will be described. The following embodiments are given in order to illustrate the present invention and are not intended to limit the present invention in any way. The present invention can be carried out in various embodiments as long as said embodiments do not depart from the scope thereof.

The documents, laid-open publications, patent gazettes and other patent documents cited in this specification are incorporated herein by reference. The present specification incorporates the contents of the specification of Japanese Patent Application No. 2006-292688, which serves as the basis for claiming the priority of the present application.

Hereinafter, a method for preparing a thin film polymer structure according to the present invention (hereinafter, referred to also as a "sheet") having a different functional substance on its each of its two sides will be described.

1. Production of a Thin Film Polymer Structure Having a Functional Substance on the A Surface and B Surface of the Film (1)

In one aspect of the present invention, a thin film is formed at an arbitrarily-shaped, soluble region at the interface between a liquid phase and a substrate body (hereinafter sometimes referred to as a "substrate") by adsorbing polyfunctional molecules thereon, polymerizing and/or crosslinking these polyfunctional molecules. Thereafter, a functional substance is bonded to the face (A surface) of the thin film, and a soluble support film is formed thereon (atop the substrate body upon which the thin film was formed). Then, said thin film and soluble support film are exfoliated from the substrate body, a functional substance identical to or different from the aforementioned functional substance is bonded to the B surface of the thin film, and the soluble support film is dissolved with a solvent. Herein, "A surface" and "B surface" mean one side and the other side of the thin film, respectively, and the A surface is described, as the face, while the B surface is described as the reverse face in this specification. In the above aspect of the present invention, for the film formed atop the substrate body, the side adsorbed to the substrate body is the B surface, and the side opposite that which is adsorbed to the substrate body is the A surface.

2. Production of a Thin Film Polymer Structure Having a Functional Substance on the A Surface and B Surface of the Film (2)

In another aspect of the present invention, a thin film is formed at an arbitrarily-shaped, soluble region at the interface between a liquid phase and a substrate body by adsorbing polyfunctional molecules thereon, polymerizing and/or crosslinking these polyfunctional molecules. Thereafter, a functional substance is bonded to the A surface of the thin film, and said thin film is exfoliated from the substrate body by dissolving the soluble region with a solvent. Then, the A surface of the exfoliated thin film is applied atop the soluble support film formed at a substrate body different from the aforementioned substrate body, a functional substance identical to or different from the aforementioned functional substance is bonded to the B surface of the thin film, and the soluble support film is dissolved with a solvent to exfoliate the thin film. The step of polymerizing and/or crosslinking the polyfunctional molecules also comprises the step of laminating polyelectrolytes having opposite charges to each other alternately to crosslink the polyelectrolytes in terms of charges.

The method of the present invention has enabled, for the first time, the thin film to be exfoliated from the substrate body (or a solid carrier) and a thin film polymer structure having a functional substance on its A surface and B surface to be obtained easily and reliably. The method of the present invention also makes it possible to manufacture large quantities of the thin film structure.

The thin film polymer structure of the present invention is a single-layer thin film or a multi-layer thin film in which polyfunctional molecules are polymerized and/or crosslinked.

The structure can be obtained as a thin film dispersion of polymer. A dispersion having the thin film polymer structure of the present invention dispersed in a liquid is encompassed in the scope of the present invention.

A thin film polymer structure to which the thin film polymer structure of the present invention is adhered by application, coating, or the like at an interface such as at least one of the surfaces selected from of the following: a tissue, an internal organ, a vascular wall, a mucous membrane, skin, etc. is also encompassed in the scope of the present invention. In addition, the scope of the present invention also encompasses thin film polymer structures that cultivate skin, a cornea, internal organ tissues, etc. atop substrate body/soluble support film/thin film polymer structure and are exfoliated along with structures.

(1) Area of an Arbitrary Shape in an Interface Between the Substrate Body and a Water Surface In the present invention, the term "interface between the substrate body and a liquid phase" refers to an interface at which the solid substrate body is in contact with a liquid such as water, an aqueous solution, or an organic solvent.

The shape of the area to which polyfunctional molecules are made to adsorb may be identical to the shape of the substrate body or a part thereof and has no specific limitation. The area may be, for example, circular, rectangular, elliptical, ribbon-shaped, cord-shaped, branched at a plurality of points, or star-shaped.

In the present invention, it is desirable to form a self-assembled monolayer (SAM) or a self-assembled bilayer (SAB) at the interface between a substrate body and a liquid phase.

The term "self-assembled monolayer (SAM)" refers to a film formed of linear hydrophobic molecules having, at a terminus, a functional group which can be bonded to the substrate body. The linear hydrophobic molecules are anchored to the surface of the substrate body via the functional group to form the monolayer. The term "self-assembled bilayer (SAB)" refers to a bilayer constructed of, for example, amphiphilic molecules containing a hydrophobic hydrocarbon chain such as a lipid, and a hydrophilic polar head group. The self-assembled bilayer (SAB) is formed by self-assembly in a hydrophilic area of the substrate body surface or in an area of the substrate body surface which has the opposite charge to that of the polar head group of the amphiphilic molecules. Alternatively, a bilayer structures formed by self-assembly of amphiphilic molecules in a hydrophobic area formed at a SAM and whose film surface becomes a hydrophilic region can also be regarded as an SAB.

Herein, the term "self-assembled layer" refers to a film spontaneously formed.

In the present invention, the substrate body may be anything which allows polyfunctional molecules to adsorb thereto with no specific limitation. Where a SAM or SAB is formed on a substrate body, the substrate body may be anything which allows the SAM or SAB to be formed thereon with no specific limitation. The substrate body may be, for example, a metal plate formed of gold, silver, platinum, copper, iron, aluminum, titanium, zinc or the like, or a flat plate having such a metal material vapor-deposited thereon. The substrate body may be entirely or partially formed of the following, either alone or in an appropriate combination: a metal material described above or an oxide cover layer thereof, silicon, silicon rubber, silica or glass, mica, a carbon material such as graphite, a polymer material such as polyethylene, polypropylene, cellophane, and elastomer, or a calcium compound such as apatite.

According to the present invention, a hydrophobic part of the hydrophobic molecules forming the SAM may be formed of linear hydrophobic molecules having, at a terminus, an SH group, a chloroalkylsilyl group, an alkoxyalkylsilyl group, a vinyl group, an amino group, a carbonyl group or the like. Usually, the hydrophobic part is formed of a saturated hydrocarbon chain having a carbon number of 4 to 40, preferably of 8 to 18. A linear hydrophobic molecule having an SH group is, for example, alkanethiol. Examples of alkanethiol include undecanethiol, dodecanethiol, and tetradecanethiol. The hydrophobic molecule may have alkene or alkyne containing an unsaturated bond, an isoprenoid backbone having a branching structure, or a steroid ring.

A SAM can be spontaneously formed on a gold substrate body by dissolving the above-described hydrophobic molecules having an SH group in a solvent such as ethanol and putting the gold substrate body into contact with, or immersing the gold substrate body in, the resultant solution. A SAM is obtained on a silicon substrate body by long-chain molecules having a vinyl group. A SAM is obtained on the surface of a silica or metal substrate body by long-chain molecules having a chloroalkylsilyl group or an alkoxyalkylsilyl group. Examples of a long-chain hydrophobic molecule having such a group include octadecyldimethylchlolosilane, trialkoxyhexadecylsilane, and octadecyltrimethoxysilane (ODMS). For example, a SAM is obtained by vapor-depositing ODMS on a silicon oxide substrate body. The term "vapor deposition" refers to heating and vaporizing a substance in a vacuum condition or a condition close to vacuum, so that a thin film of the vaporized substance is formed on the surface of a substrate body.

In the present invention, the amphiphilic molecules forming the SAB may be any type of molecules which include a hydrophobic part and a hydrophilic polar part therein. Examples of the amphiphilic molecule usable to form the SAB include lipids such as a hydrophobic phospholipid, an amino acid-based lipid, and a glycolipid, and cationic lipids such as dialkylammonium salt.

A SAB is formed as follows. A layer having a bilayer structure can be easily formed through coating by means of an organic solvent, obtained by dissolving amphiphilic molecules such as lipid molecules, to a substrate. Thereafter, a certain area is masked, and electron beam radiation or the like is performed to decompose and thus remove the bilayer structure of the non-masked area. Thus, an area having the bilayer structure is formed.

Alternatively, an SAB can be spontaneously formed as follows. A substrate body including an anionic area or a cationic area as a result of surface treatment is put into contact with, or immersed in, a dispersion of cationic lipid or anionic lipid. The SAB is formed in the area.

An SAB can also be spontaneously formed as follows. A substrate body including an area having a SAM formed thereon is put into contact with, or immersed in, a solution or a dispersion of amphiphilic molecules.

These polymer molecules can be caused to adsorb to, or chemically modify, an arbitrary area of the substrate body using the masking technology described later.

In the present invention, an area of a surface-treated substrate body, namely, an area of a SAM-formed substrate body, an area of a SAB-formed substrate body, or an area of a photoresist-formed substrate body may be formed to have an arbitrary shape using masking. A photomasking method will be described below, but a person of ordinary skill in the art can select appropriate elements for masking. The method is not limited to the method described below.

First, a resist is formed on a surface-treated substrate body. For example, a positive photoresist may be coated onto the surface-treated substrate body by a spin coater at 800 rpm for 3 seconds and then coated at 7000 rpm for 20 seconds, and heated, for example, at 110° C. for 90 seconds to be dried. The thickness of the photoresist is decreased by increasing the rotation rate and the rotation time. The heating temperature and the heating time are not limited to the above and may be appropriately altered as long as the solvent of the resist is vaporized. Next, a photomask is formed on the resist, and the resist is exposed to light. The resist may be exposed to light by radiating an electron beam, an ultraviolet ray, an X-ray or the like for 1 to 60 seconds, preferably for 5 to 20 seconds. The photomask may be, for example, a rectangular mask having a size of 10 µm×30 µm or a circular mask having a diameter of 3 µm. Next, the exposed area of the resist on the substrate body is developed and dried, whereas the non-exposed area of the resist is removed. Then, an area of the SAM or SAB which is not protected by the resist is removed by $O_2$ plasma treatment, CO plasma treatment, or reactive ion etching using halogen gas. Finally, the resist is removed by a resist-soluble solvent such as acetone, THF, or dichloromethane. Thus, an area of a desirable shape (for example, having a micropattern) which has a film structure can be formed.

In the present invention, the term "soluble region" includes, but is not limited to, a soluble polymer film in a solvent such as acetone, acetic ether, an alcohol, water, or an aqueous solution. A solvent that does not dissolve the structure of the thin film polymer structure itself must be selected. Alternatively, a solvent that does not dissolve the thin film polymer structure during processing by conditions such as temperature, pH, and ion intensity may be selected. Examples of the soluble region include those formed from, for example, a polyelectrolyte such as a polyacrylic acid or a polymethacrylic acid, polyethylene glycol, polyacrylamide, polyvinyl alcohol, a nonionic water-soluble polymer such as a polysaccharide such as starch or acetylcellulose, or a resin such as novolac or poly(N-alkyl cyanoacrylate). In the polymer solution that forms the soluble region, the molecular weight of the polymer is 1000 to 1,000,000, preferably 5000 to 500,000. The concentration of the solution is 1 to 20 wt %, preferably 2 to 10 wt %. Alternatively, a solution with a viscosity of 200 to 500 cP is desirable. The soluble region is formed by coating the abovementioned solution onto a substrate body prior to the formation of the thin film polymer structure and then drying the resultant substrate body for 10 minutes to 24 hours, preferably 1 to 12 hours. Alternatively, the method for forming the soluble region is desirably, but is not limited to, using casting or spin-coating to coat the aforementioned solution onto a substrate body, heating the coated substrate body for 90 seconds on an iron plate heated at 110° C. to volatilize the solvent.

(2) Adsorption, Polymerization, and Crosslinking of Polyfunctional Molecules

Examples of the substance to adsorb to an area (for example, an area having a SAM or SAB structure) in an interface between the aforementioned substrate body and the liquid phase, i.e., the substance that becomes the structural element of the thin film, include polyfunctional molecules such as polyfunctional monomers and polyfunctional macromers.

A polyfunctional monomer or macromer includes two or more homogeneous or heterogeneous functional groups in one molecule. Examples of the polyfunctional monomer include monomers, such as amino acids and sugars, containing a plurality of amino groups, carboxyl groups, hydroxyl groups, mercapto groups, isocyanate groups, aldehyde groups, epoxy groups, cyanuric group and the like; and monomers containing a plurality of vinyl groups such as divinylbenzene, divinylether, divinylsulfone, bismaleimide and the like. Examples of the polyfunctional macromer include proteins, polylysine, polyglutamic acid, substances obtained by hydrolysis of polystyrene/maleic acid anhydride copolymers, kitosan, alginic acid, polymer beads, a polylactic acid, a polylactic acid/glycolic acid copolymer, polycaprolactone, and the like, but can include those macromers which have terminus functional groups or multiple side chain functional groups of the repeat unit.

A mono-functional monomer or mono-functional macromer may be used in a mixture with a polyfunctional monomer or polyfunctonal macromer. For example, beads formed of a polymer such as polystyrene or poly(ε-caprolactone), or an L-lactic acid and a glycolic acid copolymer to whose surface a polyfunctional molecule (such as albumin) is adhered or whose surface is chemically-modified can also be used.

Any protein is usable; there are no particular limitations. Examples of the water-soluble protein include albumins such as BSA (bovine serum albumin) and HSA (human serum albumin), hemoglobin, myoglobin, soluble collagen, and fibrinogen. A protein which is not originally water-soluble but which coats at a support film and can be exfoliated or a protein which is not originally water-soluble but can disperse stably in a solvent when a support film is dissolved therein are usable. A protein obtained by purifying a living body-derived sample by a known method, or a peptide synthesized by a peptide synthesizer, may be used. Alternatively, a recombinant protein produced in a host such as a mammal cell, an *Escherichia coli*, or a yeast by a known method using base sequence information of genes coding a target protein, and then purified is usable (see Sambrook J and Russel D. Molecular Cloning, A Laboratory Manual, 3rd edition, CSHL Press, 2001). A substance obtained by bonding, for example, a pyridyl disulfide group, a maleimide group, or a succinimide group to a functional group of a protein such as an amino group, a carboxyl group, or a hydroxyl group via a spacer of an appropriate length is usable. A protein may be used in the form of latex beads covered with the protein.

The term "polymer beads" refers to the following types of particles: particles obtained by treating a monomer having a vinyl group with emulsion polymerization or suspension polymerization; particles granularized through O/W emulsion; particles obtained by ring-opened polymerizing a ring-shaped compound as a monomer and then emulsifying the resultant polymer with a surfactant; or particles obtained by polymerizing a polyfunctional macromer. Examples of polymer beads include latex beads formed of polystyrene-co-divinylbenzene or the like. Biodegradable polymer beads made from a polylactic acid, a polylactic acid/glycolic acid copolymer, polycaprolactone, or the like may be used as polymer beads. The polyfunctional molecule (for example, the polyfunctional monomer or macromer) may be amphiphilic. Examples of the amphiphilic molecule include polymerizable phospholipid having a diene group or a vinyl group at 1-acyl chain and 2-acyl chain, amino acid-based lipid, and sugar lipids.

The thin film (thin film polymer) may be formed of one type of molecules or a combination of a plurality of types of molecules. The combination may be a combination of a plurality of polyfunctional monomers, a combination of a plurality of polyfunctional macromers, or a combination of a polyfunctional monomer and a polyfunctional macromer. For example, polymer beads covered with a protein may be used as polyfunctional molecules.

A polyfunctional polymer adsorbs to a SAM, or SAB on a surface-treated substrate body to form a polymer thin film. Therefore, the adsorbing molecules (for example, the molecules including a hydrophobic part and forming the thin film) are arranged with the hydrophobic part being aligned along the SAM or the like. After the polyfunctional molecules adsorb, polymerization and/or crosslinking is performed as necessary to form a polymer thin film on the surface-treated substrate body (for example, on the SAM).

In order to make the polyfunctional molecules to adsorb to a SAM, the SAM-formed substrate body may be put into contact with, or immersed in, a solution or a dispersion of the polyfunctional molecules. Thus, a thin film of the polyfunctional molecules can be formed. In order to cause the polyfunctional molecules to adsorb to a SAB to form a polymer thin film, a polyelectrolyte having the opposite charge to that of the surface of the SAB may be caused to adsorb to the SAB.

In the present invention, the polyfunctional molecules can be caused to adsorb to the SAM or SAB by repeating an operation of extracting the substrate body that forms the SAM or SAB from the solution of the polyfunctional molecules at an appropriate speed, or using a gas such as air or nitrogen to sweep away the solution from the substrate body onto which the polyfunctional molecule solution was dripped, and creating the flow of polyfunctional molecule solution at the surface of the substrate body. In this case, the contact is realized using the surface tension on a gas-liquid interface. Therefore, the polyfunctional molecules can sometimes be caused to adsorb to the layer more selectively than in the liquid.

In the present invention, the term "polymerization" refers to a reaction of producing a polymer. The molecules may be polymerized by polycondensation, poly-addition, addition-condensation, ring-opening polymerization, addition polymerization (radical polymerization, anionic polymerization, cationic polymerization), solid phase polymerization by heat, photopolymerization, radio polymerization, plasma polymerization or the like.

In the present invention, the term "crosslink" refers to forming a chemical bond between some specific atoms in the linear polymer. Crosslinking forms a three-dimensional net structure.

The molecules may be crosslinked by urethane bond or urea bond by an isocyanate group, formation of a Schiff base by an aldehyde group, disulfide bond by a mercapto group or the like. Examples of the crosslinker include alkyldiimidates, acyldiazides, diisocyanates, bismaleimides, triazinyls, diazo compounds, glutaraldehyde, N-succinimidyl-3-(2-pyridyldithio)alkyonate, and bromocyan.

The crosslinking between polyfunctional macromers may be physical crosslinking such as coagulation by thermal denaturing when the macromers are proteins. When the macromers are thermoplastic polymer beads, the surface of the beads may be partially fused by heating to realize physical crosslinking. Alternatively, the polymer beads may be completely fused by heating to form a thin film having an arbitrary shape. In short, the purpose of this step is the insolubilization of the film. Accordingly, the step can include electrostatic interaction, dipole interaction, hydrogen bonding, and hydrophobic bonding, as long as the physical crosslinking fulfills this purpose. The treating conditions of a protein may be appropriately set in accordance with the properties of the protein. For example, albumin can be thermally denatured to realize crosslinking by being treated at 60 to 120° C., preferably at 70 to 100° C., for 1 to 60 minutes, preferably for 1 to 30 minutes. Polymer beads, for example, latex beads formed of polystyrene-co-divinylbenzene may be partially fused to realize crosslinking by being treated at 100 to 150° C., preferably at 110 to 120° C., for 1 second to 5 minutes, preferably for 10 to 60 seconds. Alternatively, the polymer beads may be completely fused to realize crosslinking by being heat-treated at 100 to 150° C., preferably at 110 to 120° C., for 30 seconds to 10 minutes, preferably for 1 to 5 minutes. For example, when the polymer beads are biodegradable polymer beads formed from a polylactic acid/glycolic acid copolymer, the polymer beads can be partially fused to realize crosslinking by being heat-treated at 30 to 100° C., preferably at 50 to 70° C., for 1 second to 30 minutes, preferably for 60 seconds to 20 minutes. Alternatively, the biodegradable polymer beads can be completely fused by being heat treated at 100 to 180° C., preferably 130 to 160° C., for 30 seconds to 10 minutes, preferably 1 minute to 5 minutes.

After the polymerization or crosslinking, the polyfunctional molecules may be further caused to adsorbed to, for example, the SAM- or SAB-formed substrate body on which the thin film is already formed. Polymerization or crosslinking may be repeated in this manner for further thin film formation.

According to the present invention, a polyelectrolyte may be used as a polyfunctional macromer included in the thin film. For example, a surface-treated substrate body such as a SAM or SAB is immersed in diluted solutions of polyelectrolytes (polycation and polyanion) having the opposite charges to each other alternately, so that the polyelectrolytes can spontaneously adsorb to the SAM or SAB. Thereafter, a step wherein excess polyelectrolytes are washed away is repeated. Thus, a thin film having a polycation and a polyanion alternately laminated thereon is formed. To produce a smooth thin film, the spin-coating method is used. An example is an LbL method wherein a polymer which has been dripped on a flat substrate body is alternately spread and laminated with a spin coater. Examples of the polycation include kitosan, collagen, polylysine, polyarginine, polyhistidine, ionen, poly(quaternized pyridine), polymers of diallyldialkylammonium salt, and polyallylamine. Examples of the polyanion include alginic acid, hyaluronic acid, polyglutamic acid, polymethacrylic acid, polyacrylic acid, polystyrene sulfonic acid, alkaline metal salts thereof, and alkaline earth metal salts thereof. The product of alkaline hydrolysis of an alternating copolymer of maleic anhydride and styrene can also be used.

An LbL film may also be formed by adsorbing a polyelectrolyte on a thermohardening resin such as a photoresist soluble in an organic solvent. Although the LbL method is a method for producing a thin film through the use of electrostatic bonding between polyelectrolytes having opposite charges, it is also possible to form a film through the use of hydrogen bonding and dipole interaction between polymers.

The polycation and polyanion included in the laminated layers formed by the alternate adsorption method are crosslinked in terms of charges by an electrostatic force, thus forming a thin film. Alternatively, an amino group in a polyion complex and a carboxylic acid residue in a polyion complex may be subjected to dehydration-condensation and thus crosslinked via an amide group which is a covalent bond, thus forming a thin film.

Thin films formed by the above-mentioned methods are also included in the scope of this invention.

The thin film formed at an interface between the substrate body and the liquid phase may be a single layer film or a multi-layer film.

In the present invention, the substrate body may be washed before and after the adsorption and polymerization/crosslinking of the polyfunctional molecules. The substrate body may be washed by immersing the substrate body in, or putting the substrate body into contact with, a washing liquid once or a plurality of times.

(3) Thin Film Having a Functional Substance Bonded to the A Surface Thereof

In the present invention, a functional substance may be bonded to the A surface of a thin film obtained by polymerizing or crosslinking polyfunctional molecules. Alternatively, a thin film polymer structure may also be produced by not allowing a functional substance to bond at this point, regarding a portion of the polyfunctional group of the A surface as a functional substance, exfoliating the thin film with the exfoliating method described later, and bonding the functional substance to the B surface.

The term "functional substance" refers to, for example, a substance having a molecular recognition ability such as a recognition protein or a ligand thereof, an antigen or an antibody extant on a cell membrane, a substance for promoting a specific reaction of a catalyst, an enzyme or the like, a substance involved in a specific reaction of an anti-oxidant, a radical scavenger or the like, or a group or ligand such as a carboxyl group, an amino group, a mercapto group, or a maleimide group involved in a charge or reaction. The term "functional substances" also includes substances that use the charge (electrostatic interaction) of polyelectrolytes to cause the expression of functions. Examples of functional substances include but are not limited to at least one of the following selected from the group consisting of polymers such as poly(ethyleneglycol) or a sugar chain, a protein, a peptide, a sugar chain, a biotin derivative, a polycation polyelectrolyte, and a polyanion polyelectrolyte. Examples such as those described above can be given for a polycation and a polyanion.

Functional substances can be bonded through chemical or physical methods. As a chemical bonding method, the bonding reaction between the functional molecules and the thin film may be caused by bonding via a functional group that can bond to an amino group, a carboxyl group, a hydroxyl group, a mercapto group, an isocyanato group, an aldehyde group, an epoxy group, a cyanuric group, or a vinyl group introduced into a polyfunctional monomer or macromer. For example, the bonding reaction between the functional molecules and the thin film may be caused using urethane bond or urea bond by a reaction between a hydroxyl group or an amino group and an isocyanate group, using formation of a Schiff base by a reaction between an amino group and an aldehyde group, using disulfide bond by a reaction between mercapto groups, using a reaction between a mercapto group and a pyridyldisulfide group or a maleimide group, using a reaction between a carbonyl group and a succinimide group, or the like.

The following can be used as methods for causing bonding physically: electrostatic interaction between the functional substance side and the thin film side, hydrophobic interaction, hydrogen bonding, or intermolecular force.

Alternatively, a ligand may be introduced into the thin film side or the functional substance side, so that the functional substance can be immobilized on the thin film using a complex of the ligand and an acceptor introduced into the functional substance or the thin film. Examples of the combination include biotin and avidin, a sugar chain and lectin, an antigen and an antibody, a drug and a receptor, and an enzyme and a substrate.

Examples of the enzyme include, but are not limited to, catalase, horseradish peroxidase, chymotrypsin, cytochrome, α-amylase, β-amylase, galactosidase, glycocerebrosidase, blood clotting factor, peroxidase, protease, cellulase, hemicellulase, xylanase, lipase, pullulanase, isomerase, glucoamylase, glucose isomerase, glutaminase, β-glucanase, and serine protease. The method for functional substance bonding following the introduction of a ligand or the like to the A surface of a thin film can also be carried out on a support film, or the reaction can be carried out on the dispersion that is the product of support film dissolution.

(4) Formation of the Soluble Support Film and Exfoliation of the Thin Film.

In the present invention, the soluble support film is comprised of a polymer layer soluble in a solvent such as acetone, ethyl acetate, an alcohol, water, or an aqueous solution, but is not limited to the above. A solvent that does not dissolve the thin film polymer structure must be selected. The soluble support film is formed from, for example, a polyelectrolyte such as a polyacrylic acid or a polymethacrylic acid, a nonionic water-soluble polymer such as a poly(ethyleneglycol), polyacrylamide, polyvinyl alcohol, polysaccharide such as starch or acetylcellulose, or a resin such as novolac or poly(N-alkyl cyanoacrylate). In the polymer solution used to produce the soluble support film or the soluble region, a solution with the following properties is desirable: a polymer molecular weight of 1000 to 1,000,000, preferably 5000 to 500,000, and a concentration of 1 to 20 wt %, preferably 2 to 10 wt %. The soluble support film is formed by applying the abovementioned solution to a substrate body with a thin film polymer structure formed thereon and then drying the resultant film for 10 minutes to 24 hours, preferably 1 to 12 hours. Methods for applying the abovementioned solution to the substrate body include, but are not limited to, casting and spin-coating. A pair of tweezers or the like is used to exfoliate the soluble support film and the thin film polymer structure from the substrate body. At this point, the thin film can be simultaneously exfoliated and transferred to the support film by a secondary bonding force such as electrostatic interaction, hydrogen bonding, or Van der Waals' force in the gap between the soluble support film and the thin film polymer structure. In contrast, by dissolving the soluble region atop the substrate body, a dispersion created when the thin film disperses in a liquid can be obtained. At this point, the size of the dispersion is sufficient to leave stationary the substrate body upon which the thin film polymer structure is formed. In addition, the dispersion can be exfoliated from the substrate body by leaving the substrate body at rest in a container that is insoluble to the solvent. By scraping the four corners of the formed substrate with a sharp object such as an injection needle, the substrate can be removed more quickly.

(5) Bonding of the Functional Substance to the B Surface of the Thin Film on the Support Film Side, Dissolution of the Support Film In the present invention, the structure can be the structure that was transferred to the soluble support film or the intended interface, and the B surface is placed so that it is immersed or floats so as to contact the interface between the substrate body and the liquid phase. At this point, the soluble support film can allow the aforementioned functional substance to bond in the insoluble or poorly-soluble solution. Alternatively, a thin film polymer structure may also be produced by regarding a portion of the polyfunctional group of the B surface as a functional substance without allowing a functional substance to bond.

For example, when a polyacrylic acid is used as a support film, by immersing the support film in an aqueous solution with a pH of 1 to 6, preferably a pH of 3 to 5 and a salt concentration of 10 mM to 1M, preferably 100 mM to 500 mM, the functional substance can be caused to react without dissolving the polyacrylic acid or before the polyacrylic acid dissolves. Methods are not, however, limited to the foregoing. As a method for chemically bonding the functional substance to the B surface of the thin film, bonding can be caused via a functional group that can bond to an amino group, a carboxyl group, a hydroxyl group, a mercapto group, an isocyanato group, an aldehyde group, an epoxy group, a cyanuric group, or a vinyl group introduced into a polyfunctional monomer or macromer. For example, the bonding reaction between the functional molecules and the thin film may be caused using urethane bond or urea bond by a reaction between a hydroxyl group or an amino group and an isocyanate group, using formation of a Schiff base by a reaction between an amino group and an aldehyde group, using disulfide bond by a reaction between mercapto groups, using a reaction between a mercapto group and a pyridyldisulfide group or a maleimide group, using a reaction between a carbonyl group and a succinimide group, or the like. The following can be used as methods for causing bonding physically: electrostatic interaction between the functional substance and the thin film, hydrophobic interaction, hydrogen bonding, or intermolecular force. Alternatively, a ligand may be introduced into the thin film side or the functional substance side, so that the functional substance can be immobilized on the thin film using a complex of the ligand and an acceptor introduced into the functional substance or the thin film. Examples of the combination include biotin and avidin, a sugar chain and lectin, an antigen and an antibody, a drug and a receptor, and an enzyme and a substrate. The abovementioned method for functional substance bonding following the introduction of a ligand or the like to the B surface of a thin film can also be carried out on a support film, and the reaction can be carried out on the dispersion that is the product of support film dissolution.

After causing a functional substance to bond, a dispersion liquid of a thin film polymer structure having a functional substance on the A surface and B surface thereof can be obtained by dissolving the support film. The functional substance bonded to the A surface and B surface can be either identical or different. At this time, the unattached functional substance and the dissolved support film can be removed through centrifugal separation and filtering or ultrafiltration. The term "different" means divergent from one another and indicates that the functional substance bonded to the A surface and the functional substance bonded to the B surface are dissimilar in terms of type and properties. For example, a relationship between biotin and avidin, a sugar chain and lectin, an antigen and an antibody, a drug and a receptor, or an enzyme and a substrate, is a relationship between a substance and a coupling substance thereto and can be said to be two different functional substances. In contrast, when an identical functional substance is bonded to the A surface and the B surface, for example, an identical bonding partner can be bonded to the functional substance on the A surface and the B surface. In this instance, if the bonding partner of a functional substance has a single reactive site, a structure wherein the bonding partner is bonded to the A surface and the B surface via the functional substance can be formed. If the bonding partner of a functional substance has two or more reactive sites, the structure forms an aggregate with the bonding partner via the functional substance. In addition, if a great quantity of either the functional substance or its bonding partner is inserted, the disaggregation of the aggregate can be induced. Even if a functional substance is not bonded to the A surface and the B surface, if the LbL method is used so that, for example, the A surface is a polycation and the B surface is a polyanion, a thin film polymer structure can be produced by regarding the dissociable group of the structure as a functional substance.

In the present invention, the term "biotin derivative" refers to biotin having a functional group such as an amino group or a carboxyl group or an active ester group such as pyridyldisulfide group or a succinimidyl group bonded thereto.

The sheet of the present invention can be used as a drug carrier (for example, a functional carrier or a platelet substitute in a drug delivery system). When the abovementioned modification is used as a drug carrier, the modification may be, for example, (a) drugs, (b) substances including a site specifically recognizing a target tissue/cell (specific recognition substances), or (c) substances for stabilizing the structure in the body. Specific examples of these functional substances are as follows:

(a) Drugs: anti-inflammatory drugs, hemostatic agents, vasodilating agents, thrombolytic agents, anti-arteriosclerosis agents, etc.

(b) Specific recognition substances: collagen, laminin, VCAM-1, selectin, fibrin, etc.

(c) Substances for stabilizing the structure: poly(ethyleneglycol), polyvinylpyrrolidone, polyvinylalcohol, polysaccharides, polyglutaminic acid, etc.

An arbitrary functional substance may be bonded via, for example, urethane bonding or urea bonding between a hydroxyl group or an amino group of the arbitrary substance and an isocyanate group of the structure; activating a carboxyl group of the arbitrary substance and bonding an amino group of the resultant structure with an amide group; bonding an amino group of the arbitrary substance and an amino group of the structure at a Schiff base through the use of glutaraldehyde; bonding a carboxyl group of the arbitrary substance to an amino group of the structure or hydroxyl group of the structure through amide bonding or ester bonding; a method wherein the arbitrary substance is a polysaccharide and a hydroxyl group thereof is crosslinked with an amino group of the structure after the cyanogen bromide forms imide carbonate; and disulfide bonding between a mercato group of the arbitrary substance and an activated mercapto group of the structure. Alternatively, a crosslinker such as alkyldiimidates, acyldiazides, diisocyanates, bismaleimides, triazinyls, diazo compounds, glutaraldehyde, N-succinimidyl-3-(2-pyridyldithio)alkyonate, and bromocyan can be used to facilitate crosslinking with the corresponding functional group. Still alternatively, when the arbitrary substance is hydrophobic, the arbitrary substance may be bonded to a hydrophobic area of the thin film structure by hydrophobic interaction. When the arbitrary substance is hydrogen-bondable, the arbitrary substance may be bonded to a hydrogen-bondable area of the structure by a hydrogen bond. When the arbitrary substance is charged, the arbitrary substance may be bonded to an area of the structure having the opposite charge by electrostatic interaction.

In yet another separate embodiment of the present invention, an identical or different functional substance is bonded to the B surface of the thin film polymer structure that is applied to the soluble support film formed on the substrate body. This structure is, along with the support film or the support film and the substrate body, adsorbed to the arbitrary interface and then the support film is dissolved. In this way, the substrate body is also exfoliated and the thin film polymer structure can be transferred to the interface side.

For example, as shown in the examples, if polyvinyl alcohol is spin coated atop a polypropylene substrate, a polyvinyl alcohol sheet is exfoliated from the polypropylene substrate in acetone, and the polyvinyl alcohol sheet is mounted (re-adsorbed) atop the silicon rubber substrate. If the polyvinyl alcohol sheet is dissolved with water when the polyvinyl alcohol sheet with a thin film polymer structure mounted thereon is applied to the skin, the thin film polymer structure can be transferred to the skin. At this point, in addition to silicon rubber, a general-purpose polymer material such as polyethylene or polypropylene or an elastomer or rubber having elasticity may be used as the substrate. The interface to which adhesion will be made can be the surface of a biological site such as a cell, a tissue, an internal organ, a vascular wall, a mucous membrane, a cornea, skin, hair, or a nail. A structure may also be obtained by cultivating skin, a cornea, etc. on thin film polymer structures and being exfoliated along with said structures. For example, a thin film polymer structure may be obtained by cultivating skin, a cornea, internal organ tissues, etc. atop substrate bodies/ soluble support films/thin film polymer structures and being exfoliated along with said structures. The state of thin film polymer structures that were attached to the arbitrary interface by application, coating, or the like may differ from that of thin film polymer structures dispersed in liquid. For example, the former are shapes that spread out and are fixed atop the interface, while the latter are dynamic shapes that spread out, roll up into a ball, or fold. There are also instances of the former in which the structure of functional substances changes due to interaction with the interface.

Hereinafter, the present invention will be described in more detail by way of specific examples, but the present invention is not limited to these specific examples.

EXAMPLE 1

Production of an Albumin Nanosheet Having Different Functional Substances on the A Surface and B Surface Thereof

EXAMPLE 1-1

Production of an Albumin (HSA) Nanosheet on a Hydphilic/hydrophobic Micropatterned Substrate Octadecyltrimethoxysilane (ODMS) was vapor-deposited on a silicon oxide ($SiO_2$) substrate. Then, a positive photoresist was coated thereon by a spin coater (800 rpm, 3 s+7000 rpm, 20 s), and was heated to be dried (100° C., 90 s). A photomask (rectangular, 10 μm×30 μm) was formed on the resultant substrate, and the substrate was irradiated with UV (7 s). After development and drying, a resist pattern was obtained on the substrate. A part of the ODMS not protected by the resist was removed by $O_2$ plasma treatment (30 s), and then the resist was removed by acetone. Thus, a hydphilic/ hydrophobic micropatterned substrate (ODMS-SiO$_2$ substrate) was produced (FIG. 1).

To the HSA, LC-SPDP (10 equivalent) was added (room temperature, 20 minutes), and the resultant substance was purified by GPC (gel permeation chromatography), thereby obtaining PD-HSA. Next, the PD group was reduced by dithiothreitol (DTT). Based on the freed 2-thiopyridone (2TP, ε=8.1×10$^3$ M$^{-1}$cm$^{-1}$, 343 nm), it was confirmed that 7.4±1.2 molecules of PD group were bonded to one molecule of rHSA. After purification by GPC, rHSA-SH was obtained. The ODMS-SiO$_2$ substrate was immersed in rhodamine labeled HSA-SH (room temperature, 1 hour). After removal of the nonadsorbed HSA-SH, the ODMS-SiO$_2$ substrate was immersed in acetate buffer solution containing copper ions ([Cu$^{2+}$]=100 µM, room temperature, 12 hours) and disulfide crosslinked, thereby forming an HSA nanosheet.

EXAMPLE 1-2

HSA Nanosheet Exfoliation Using Polyvinyl Alcohol (PVA) as a Support Film

Figure 2:
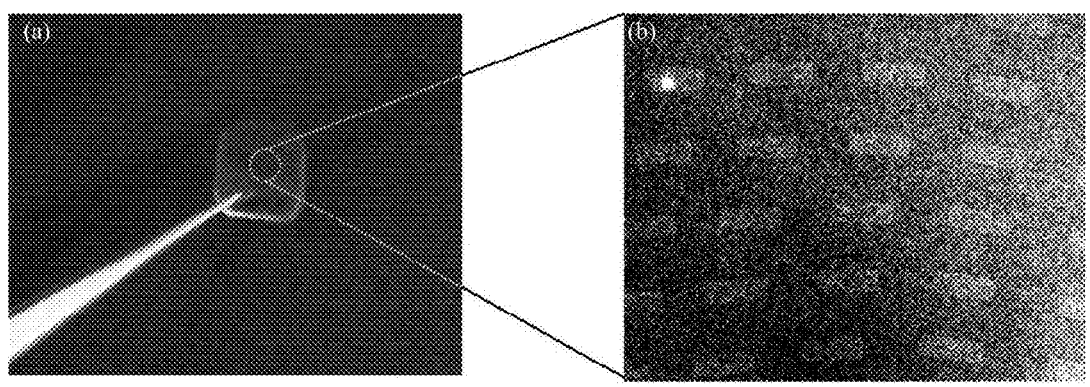
FIG. 2 shows an HSA nanosheet atop the PVA film as seen through the following: (a) light microscope and (b) fluorescent microscope.

After casting the PVA solution (2.5 wt %) on the substrate, the HSA nanosheet was left stationary in a desiccator (room temperature, 12 hours) to dry. After being dried, the PVA film was easily exfoliated with tweezers (FIG. 1, FIG. 2a). Then, the PVA film or ODMS-SiO$_2$ substrate where the PVA film was exfoliated was observed with a fluorescent microscope and an HSA nanosheet arranged in a pattern was observed on the PVA (FIG. 2b). After exfoliation of the PVA film, an HSA nanosheet could not be confirmed on the substrate. This is a result of the fact that, during drying, there is no hydrophobic interaction between the HSA nanosheet and the ODMS and that only Van der Waals force exists between the two. In contrast, since electrostatic interaction is induced between the HSA nanosheet and the PVA film, the nanosheet pattern was transferred to the PVA film. Accordingly, it was confirmed that PVA can be used to easily exfoliate the nanosheet. It was shown that this method can be used to modify the A surface and the B surface of the sheet with different functional substances using a PVA film as a support film.

EXAMPLE 1-3

Latex Bead Modification of the HSA Nanosheet B Surface

7-Chloro-4-nitrobenzo-2-oxa-1,3-diazole(NBD-Cl) was reacted with HSA, thereby obtaining NBD-labeled HSA. Latex beads (LB) (diameter 100 nm) were added to NBD-labeled HSA (room temperature, 2 hours), and the product was ultracentrifuged and redispersed, thereby obtaining (NBD)HSA-LB. With the amino group of the lysine residue of the adsorbed HSA as a target, LC-SPDP (room temperature, 20 minutes) and DTT (room temperature, 10 minutes) were added in sequence, thereby obtaining SH-(NBD)LB.

Figure 3:
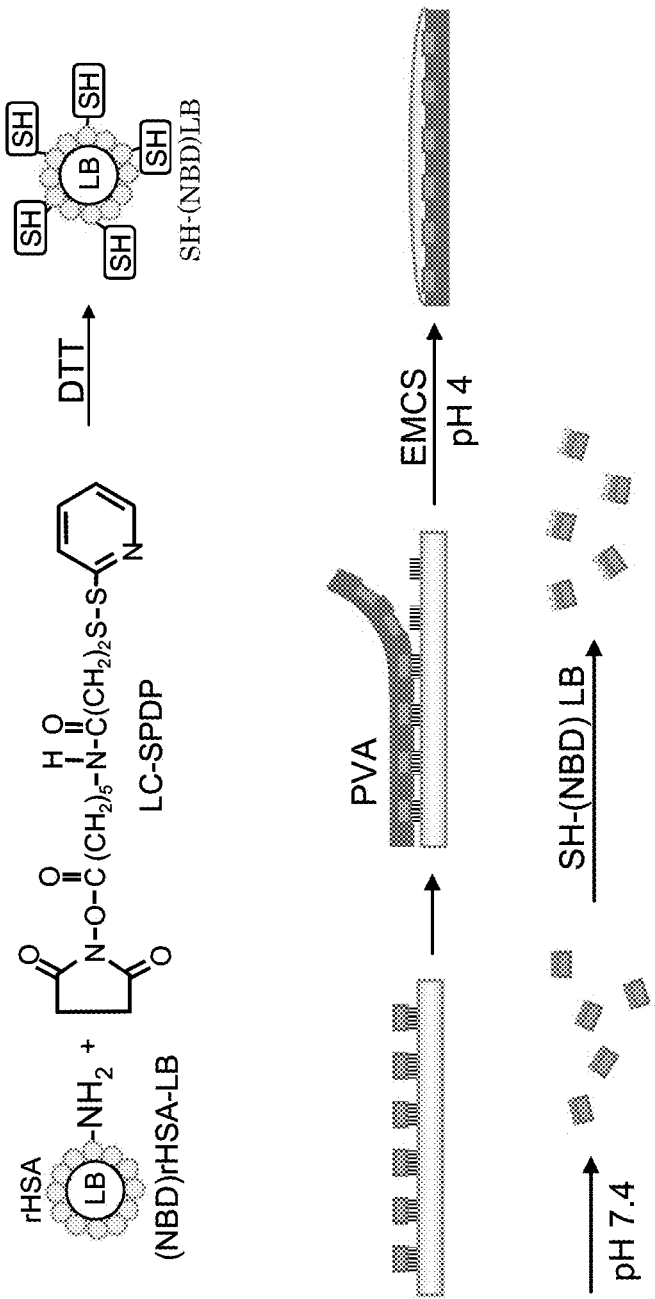
FIG. 3 shows an outline of the process wherein NBD-labeled latex beads bond to the surface of the HSA nanosheet.

A rhodamine (E$_x$=545 nm, E$_m$=580 nm)-labeled HSA nanosheet was exfoliated at the PVA film and then turned over as is. Directly after coating of a phthalate buffer (pH 4.0), N-[ε-maleimido caproyloxy] succinimide ester (EMCS) (room temperature, 5 minutes) was added, and a maleimido group was introduced. After the PVA film was dissolved by PBS, a NBD (E$_x$=475 nm, E$_m$=540 nm)-labeled SH-LB was added and LB were bonded to the B surface of the HSA nanosheet (FIG. 3).

When the LB-modified HSA nanosheet was activated at 543 nm and observed with a confocal microscope at a detected wavelength of (>560 nm), the entirety of the curved sheet surface emitted a red light. Then, when the LB-modified HSA nanosheet was activated at 458 nm and the detected wavelength was set to (505 to 530 nm) for the NBD alone, the emission of a yellow light in the shape of the sheet was confirmed. However, notable quenching (fluorescent energy transfer) of the curved section could be observed. This showed that latex beads exist on the B surface of the curved section.

EXAMPLE 1-4

AFM Observation of the HSA Nanosheet

Figure 4:
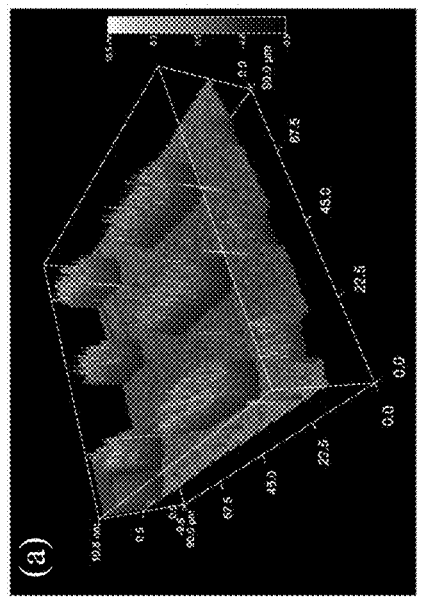
FIG. 4 shows an HSA nanosheet constructed upon a substrate as seen through an atomic force microscope.
Figure 4:
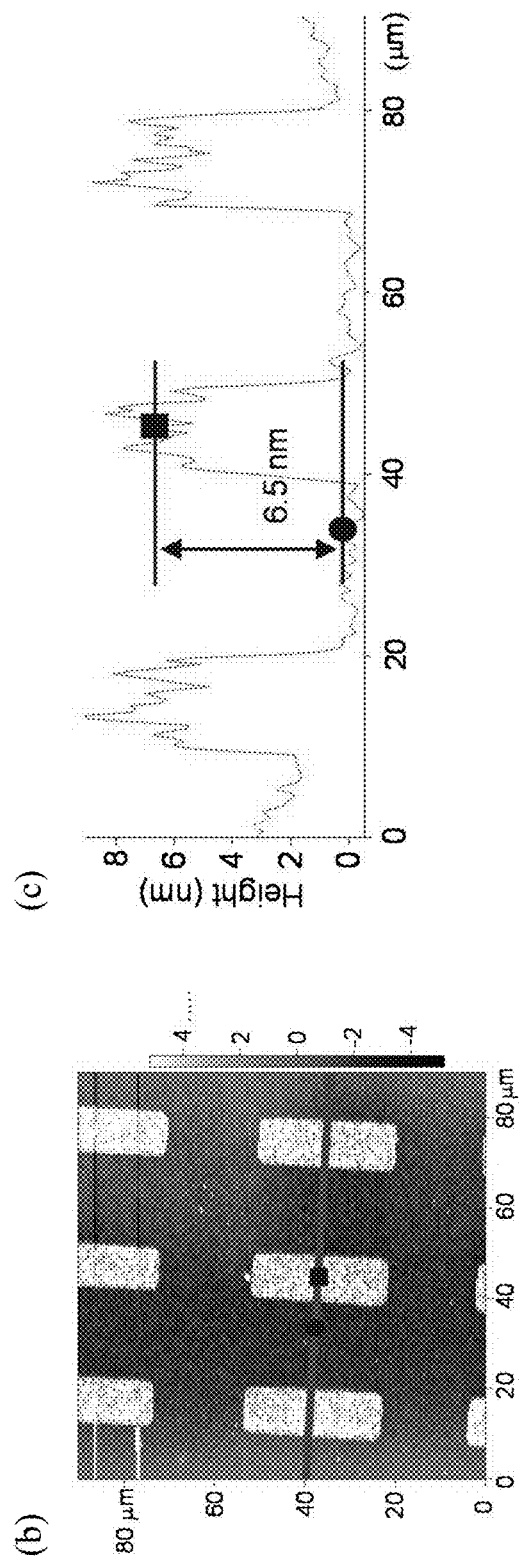

After the HSA nanosheet was formed at the ODMS-SiO$_2$ substrate, it was confirmed through observation via an atomic force microscope, as with observation via a fluorescent microscope, that HSA was selectively adsorbed only at a rectangular (10×30 µm) hydrophobic ODMS region site (FIG. 4a). Consequently, calculations based on height difference between the SiO$_2$ surface and the HSA nanosheet revealed that the film thickness was 6.5 nm. Similarly, the film thickness of the ODMS region of the nonadsorbed HSA was 3.5 nm, and this difference was used to confirm an HSA nanosheet film thickness of approximately 3 nm (FIG. 4b, c). Accordingly, the HSA nanosheets were almost all HSA molecules (equilateral triangle-shaped column; equilateral triangle, 1 side=8 nm, height=3 nm) with one layer being two-dimensionally crosslinked.

EXAMPLE 2

Production of an HSA-Adsorbed Latex Bead Heat Fusion Nanosheet ((HSA) LB Sheet) Having a Different Functional Substance on Each of the Two Sides Thereof

EXAMPLE 2-1

A Poly(Acrylic Acid) (PAA) Support Film of the (HSA)LB Sheet is Exfoliated

At the DMS region on the dodecyltrimethoxysilane (DMS) pattern substrate (DMS-SiO$_2$), an (HSA)LB was selectively adsorbed and subjected to heat fusion, thereby obtaining a nanosheet. On said substrate, polyacrylic acid (weight-average molecular weight 450,000, 50 mg) was dissolved in methanol/water mixed solvent (9/1) (volume/volume); a sheet was cast on a substrate that formed an (HSA)LB and dried overnight. Thereafter, the PAA support film was exfoliated from the substrate, and a flexible yet strong transparent film was thereby obtained. The PAA was able to be exfoliated while supporting the (HSA)LB sheet as a support film.

Figure 5:
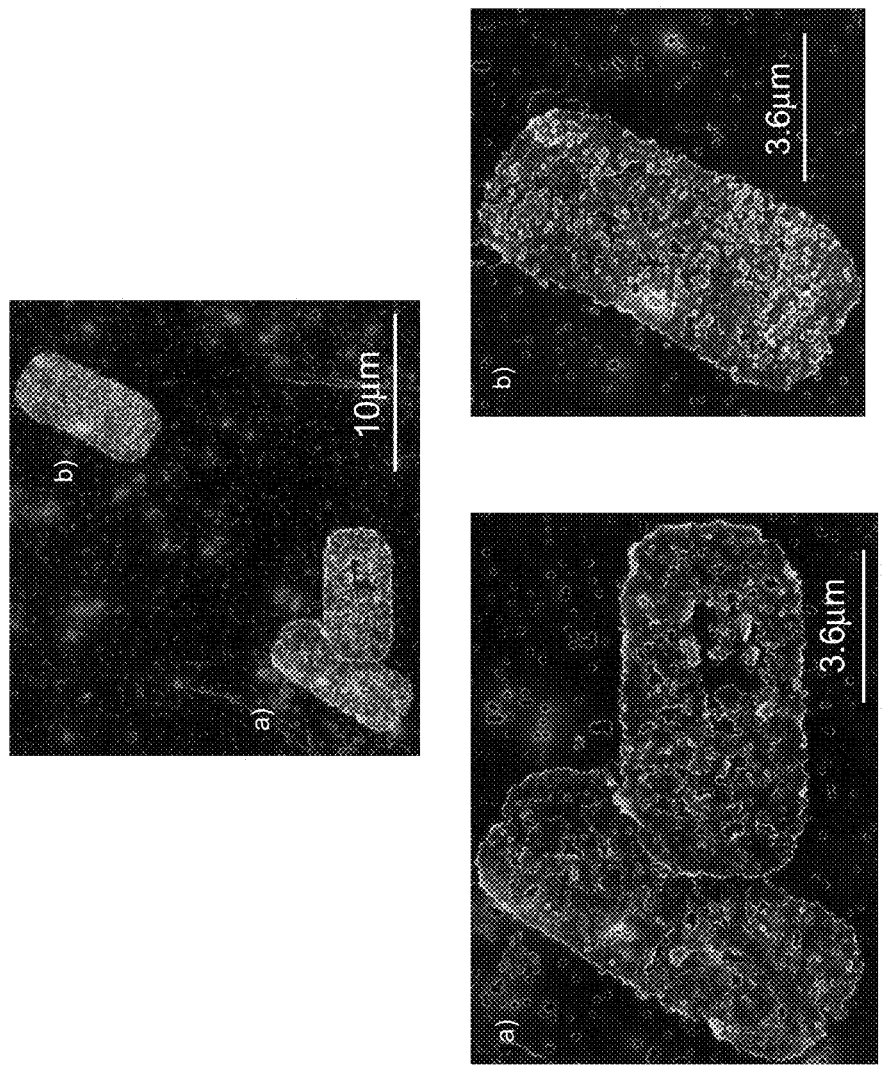
FIG. 5 shows an (HSA)LB sheet as seen through a scanning electron microscope.

A membrane filter that captured the (HSA)LB sheet was observed with a field emission scanning electron microscope (Hitachi S-4500, 10 kV, osmium tetroxide coated). Since the surface in FIG. 5(a) is smooth, it is believed that said surface is the substrate side (B surface) of when the sheet is formed. Since the texture of particles appears on the surface of FIG. 5(b), it is believed that said surface is the dispersion fluid side (A surface) of when the sheet is formed.

EXAMPLE 2-2

Figure 6:
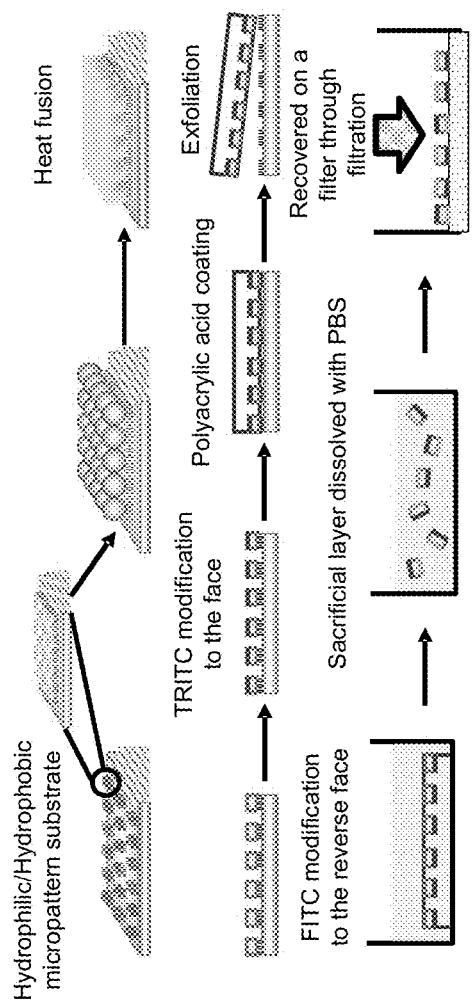
FIG. 6 shows the production method for an (HSA)LB sheet having a different functional material on its A and B surfaces.

Production of an (HSA)LB Sheet Modified with Different Fluorescent Molecules on the A Surface and B Surface Thereof (FIG. 6)

0.1 normal aqueous sodium hydroxide 300 μL was added to tetramethylrhodamine 5-(and-6-)-isothiocyanate (TRITC) (5 mg) and the product was agitated and dissolved. Then, phosphate buffer saline 900 μL was added to the resultant product, thereby neutralizing it. Next, 2 μL of the resultant product was added to phosphate buffer saline, resulting in 5 mL of liquid, and 3.76 μmol/L of TRITC aqueous solution was thereby obtained. In a 10 mL vial, the substrate upon which the (HSA)LB sheet was formed was left stationary, and 1 mL of TRITC aqueous solution was added. Then, the substrate was immersed for 20 minutes in TRITC aqueous solution and TRITC was bonded to the HSA of the A surface. Next, the (HSA)LB sheet was washed with distilled water and then dried.

Polyacrylic acid (weight-average molecular weight 450,000, 50 mg) was dissolved in a methanol/water mixed solvent (9/1) (volume/volume), then the resultant solution was cast on the (HSA)LB sheet formed substrate and dried overnight. Next, a polyacrylic acid support film was exfoliated from the substrate; and a TRITC-modified (HSA)LB sheet was thereby exfoliated.

0.1 normal aqueous sodium hydroxide 300 μL was added to fluorescein-4-isothiocyanate (FITC) (5 mg) and the product was agitated and dissolved. Then, phosphate buffer saline 900 μL was added to the resultant product, thereby neutralizing it. Next, 2 μL of the resultant product was added to a phthalate buffer saturated with sodium chloride, resulting in 5 mL of liquid, and 4.28 μmol/L of TRITC aqueous solution was thereby obtained. The sheet was placed inside a 10 mL vial so that its B surface faces upward; 1 mL of FITC aqueous solution was gradually added and the resultant product left stationary; and the FITC was bonded to the B surface of the sheet. Following the reaction, the supernatant was removed, phosphate buffer saline was added, and polyacrylic acid was dissolved.

The dispersion of the nanosheet of which both sides were modified with (HSA)LB was pressure filtered using a membrane filter (pore diameter 0.4 μm) and $N_2$ gas. Thereafter, the filter was washed with distilled water, and a nanosheet of which both sides were modified with (HSA)LB was thereby obtained (FIG. 6).

Figure 7:
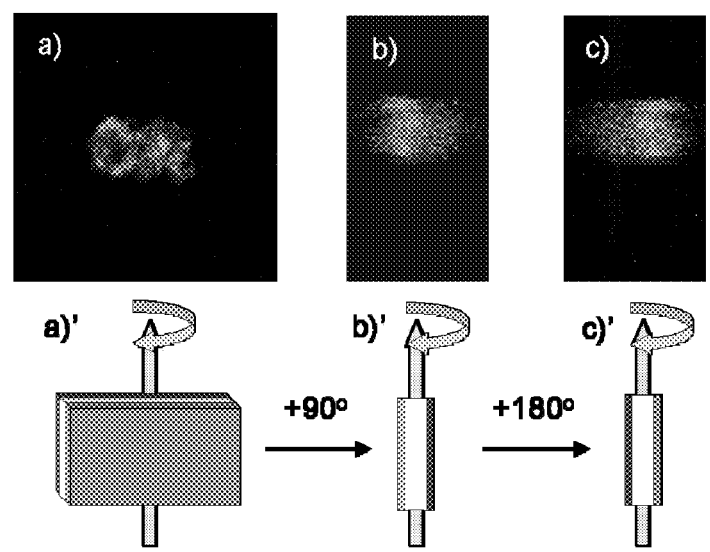
FIG. 7 shows an (HSA)LB sheet having a different functional material on its A and B surfaces as seen through a confocal laser microscope and an explanatory diagram of same.

A phosphate buffer (pH 7.6) was dripped onto the membrane filter used to recover the (HSA)LB sheet onto whose A surface and B surface the TRITC or FITC was bonded. Thereafter, the (HSA)LB sheet was applied to a glass plate. The (HSA)LB sheet was transferred to the glass plate and then fixed with agar. Observation with a confocal microscope revealed that rhodamine and FITC were bonded without mixing to the A surface and the B surface of the (HSA)LB sheet, respectively. It was confirmed that the face and reverse face of the (HSA)LB sheet reacted separately to the fluorescent substance (FIG. 7). Accordingly, it was proven that a functional substance can be bonded to the A surface and the B surface of the (HSA)LB sheet with the amino group (HSA derived) of the (HSA)LB surface as a target if the PAA film is hard to dissolve due to conditions thereof (low pH, high ion strength).

EXAMPLE 3

Production of a Layer-by-layer (LbL) Nanosheet Having a Different Functional Substance on the A Surface and B Surface Thereof

EXAMPLE 3-1

Production of an LbL Nanosheet

Figure 8:
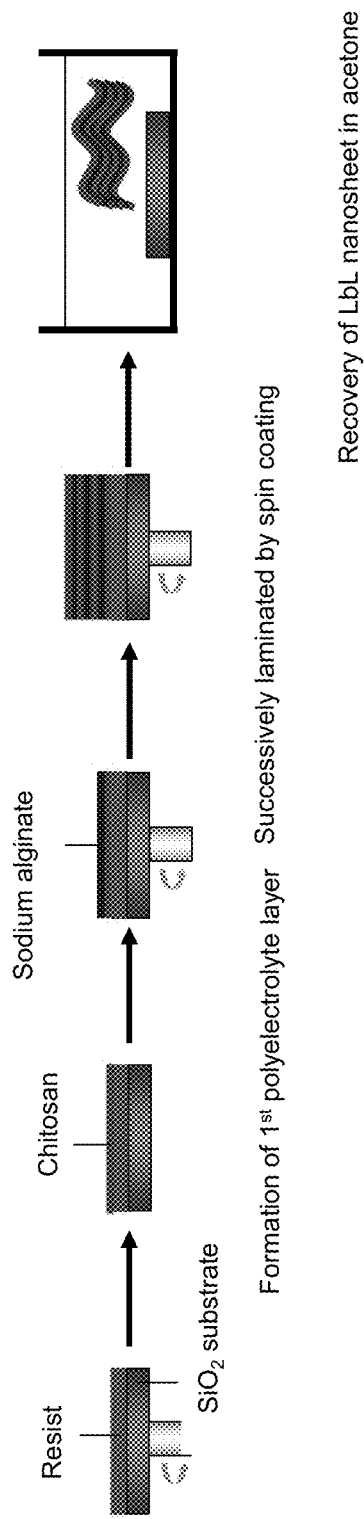
FIG. 8 shows the LbL nanosheet production method.

In the present example, an LbL nanosheet was produced by the following steps (FIG. 8).
1. Resist was spin coated (800 rpm, 3 seconds/7000 rpm, 20 seconds) as a support film onto a silicon wafer (2 cm×2 cm).
2. The silicon wafer was immersed in a chitosan aqueous solution ($M_w$: 88 kDa, 1 mg/mL, 1% acetic acid/0.5M NaCl) at room temperature for 20 minutes.
3. The substrate surface was washed with distilled water (room temperature, 1 minute) and then dried with nitrogen gas.
4. Sodium alginate ($M_w$: 106 kDa, 1 mg/mL, 0.5 M NaCl) was spin coated onto the surface of the substrate (4500 rpm, 15 seconds), then distilled water was spin coated twice onto the surface of the substrate, which was then washed.
5. Chitosan is spin coated in accordance with the conditions in step 4.
6. Hereinbelow, steps 4. through 6. above are repeated, the LbL nanosheet fixed substrate comprised of 21 layers is produced, the support film is dissolved in acetone, and the LbL nanosheet is exfoliated and then recovered.

EXAMPLE 3-2

LbL Nanosheet Observation

Figure 9:
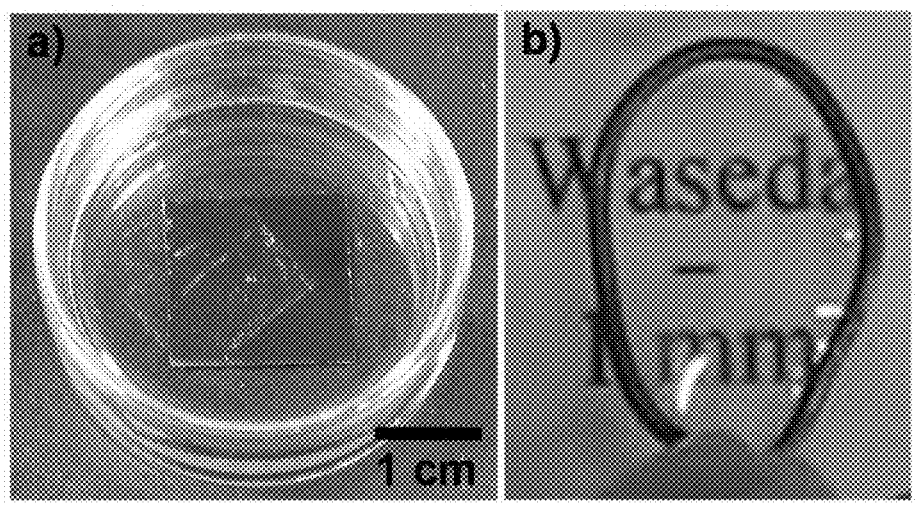
FIG. 9 shows an LbL nanosheet.

When the substrate alternatively laminated by spin-coating was immersed in acetone, only the soluble resist layer was gradually dissolved by the acetone. From the border of the substrate, the gradual exfoliation of a colorless, transparent LbL nanosheet could be observed. Further, upon being left stationary (approximately 20 minutes), the shape of a substrate was completely maintained and the LbL nanosheet with an aspect ratio exceeding 1,000,000 was successfully exfoliated (FIG. 9a). The exfoliated sheet can be scooped with a metal frame and extracted in atmosphere. The sheet did not fracture even when dried (FIG. 9b).

Figure 10:
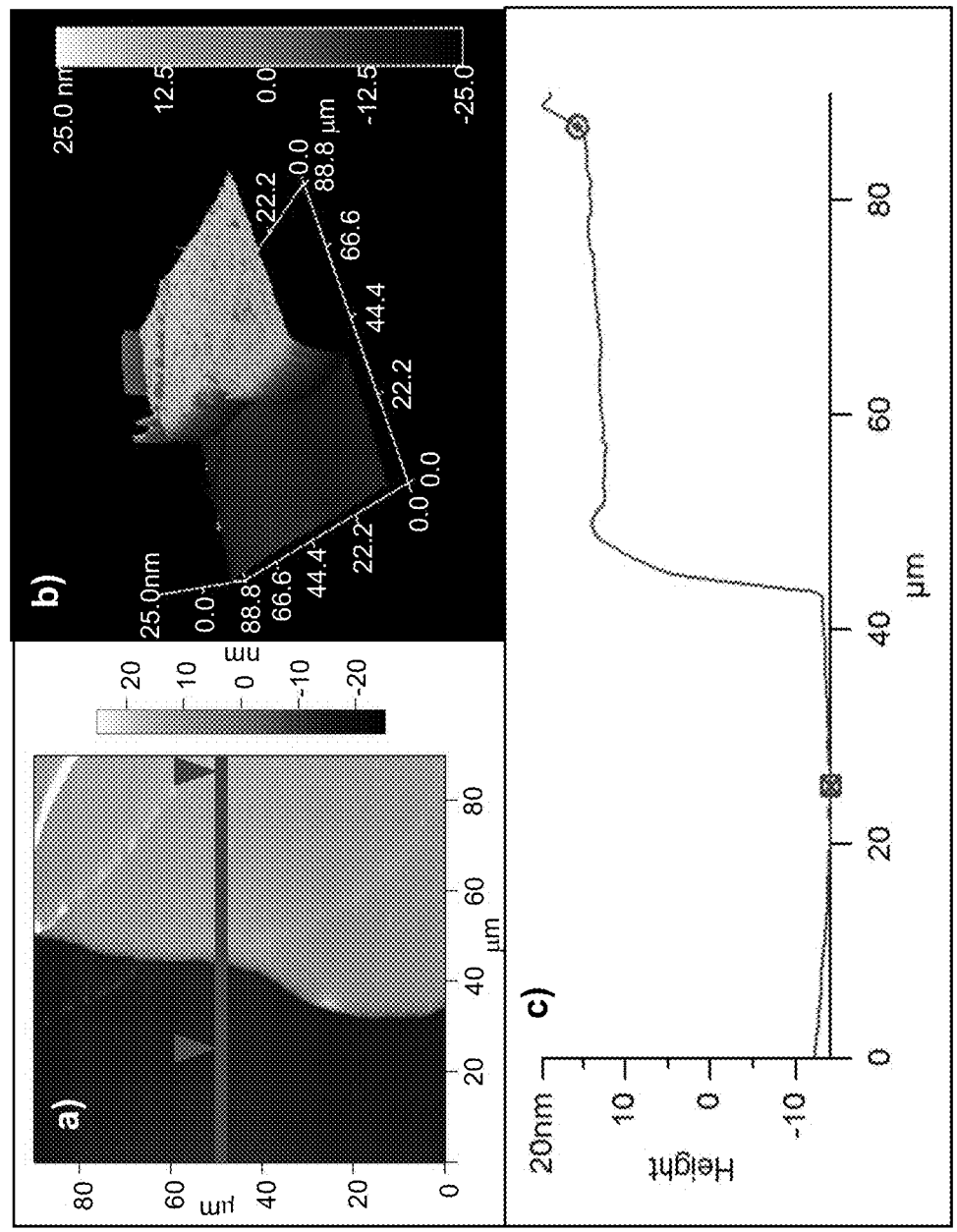
FIG. 10 shows LbL nanosheet readsorbed upon an SiO$_2$ substrate as seen through an atomic force microscope.
Figure 11:
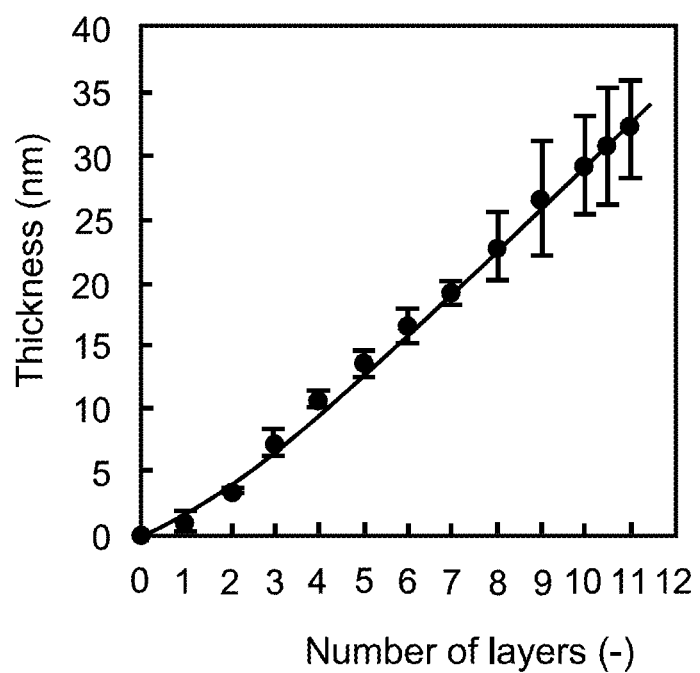
FIG. 11 shows an ellipsometric analysis of the relationship between LbL nanosheet thickness and the number of LbL method.

When the exfoliated LbL nanosheet was adsorbed to the surface of another $SiO_2$ substrate and observed with an atomic force microscope, it was observed that the surface of the LbL nanosheet was extremely smooth as that of the $SiO_2$ substrate (FIG. 10 a,b). It is believed that this is the result of polymer electrolyte horizontal diffusion that occurs in conjunction with a mechanical reaction specific to the spin-coating method. Reduction of electrolyte interaction between polymer chains within the LbL nanosheet due to the masking effect of side chains at the polymer electrolyte associated with NaCl addition is also believed to contribute to enhanced smoothness. When the height difference between the $SiO_2$ surface and the LbL nanosheet was measured, it was confirmed that the film thickness was 30.2±4.3 nm (FIG. 10c). It was confirmed by ellipsometry that this thickness is almost the same as that of the LbL film (30.7±4.5 nm) comprised of the 10.5 pair and produced without using resist on the SiO$_2$ substrate (FIG. 11).

EXAMPLE 3-3

Figure 12:
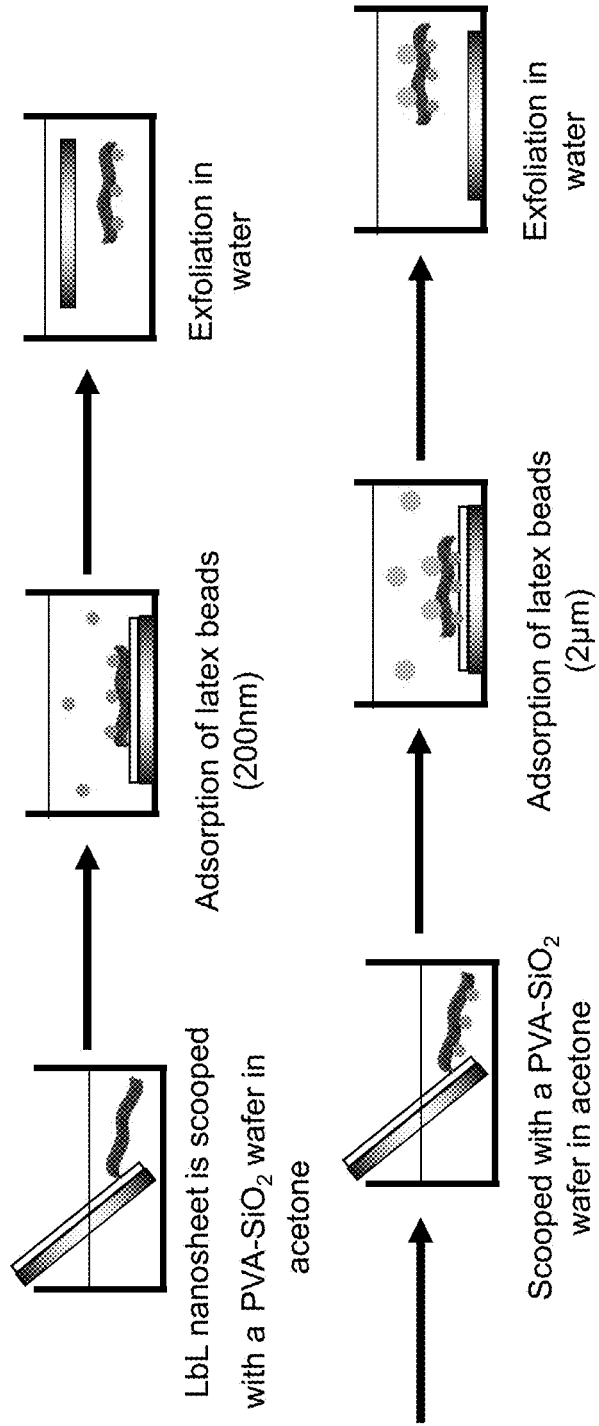
FIG. 12 shows a method for modifying the A and B surfaces of an LbL nanosheet that uses a water-soluble support film with a different functional substance on each surface.

Production of an LbL Nanosheet Having Different Functional Substances on the A Surface and B Surface Thereof that Uses a Water Soluble Support Film In the present example, an LbL nanosheet having different functional substances on the A surface and B surface thereof was produced by the following steps (FIG. 12).
1. Approximately 1 mL of a polyvinyl alcohol (PVA) aqueous solution was dripped onto a0 SiO$_2$ substrate, which was then dried.
2. An LbL nanosheet was adsorbed to the surface of a PVA solid phase SiO$_2$ substrate.
3. A substrate to which a nanosheet was adhered was immersed (room temperature, 15 minutes) in a dispersion liquid (1 mg/mL, pH 4) having latex beads (LB) with a particle diameter of 200 nm.
4. At the A surface, a 200 nm LB-modified nanosheet was exfoliated by dissolving a PVA with a phosphate buffer having a pH of 7.0.
5. The nanosheet exfoliated in 4. above was inverted and then, with its B surface facing up, readsorbed to the PVA solid phase SiO$_2$ substrate.
6. An A surface-modified substrate produced in 5. above to which a nanosheet was adhered was immersed (room temperature, 15 minutes) in a dispersion liquid (1 mg/mL, pH 4) having LB with a particle diameter of 2 µm.
7. Hereinbelow, by dissolving the PVA with a phosphate buffer having a pH of 7.0 in accordance with the method in 4. above, the LbL nanosheet modified with LB having different particle diameters on the A surface and B surface thereof is exfoliated and then recovered.

EXAMPLE 3-4

LB-modified LbL Nanosheet Observation

Figure 13:
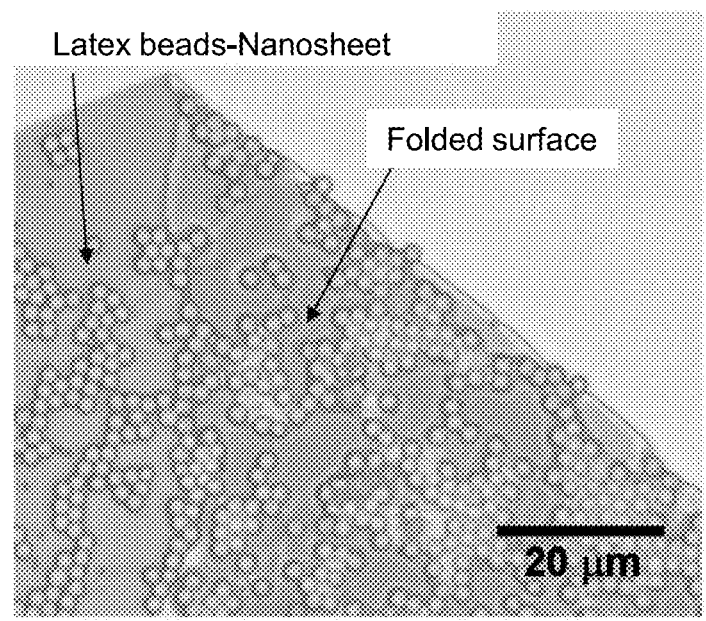
FIG. 13 shows a latex bead-modified LbL nanosheet as seen through a light microscope.

When a PVA substrate to which an LbL nanosheet was adsorbed was immersed in an LB dispersion liquid ([suspension]=5 mg/mL, pH 4) with a particle diameter of 2 µm, and LB were selectively bonded on the A surface of the nanosheet, it was observed that the structure color of the nanosheet having the fold of the nanosheet border as the boundary was different and that the LB group on the folded surface was covered by the nanosheet. It was confirmed that, in particular, the structure color of the nanosheet at the periphery of the LB group on the folded surface is identical to the structure color of the surface that was not folded (FIG. 13). It is believed that the reason for the above is that LB particles are localized on the interior of smooth thin films like nanosheets and that thin film interference is partially suppressed as a result. Due to the above, only the A surface of the nanosheet was selectively modified successfully with LB.

Figure 14:
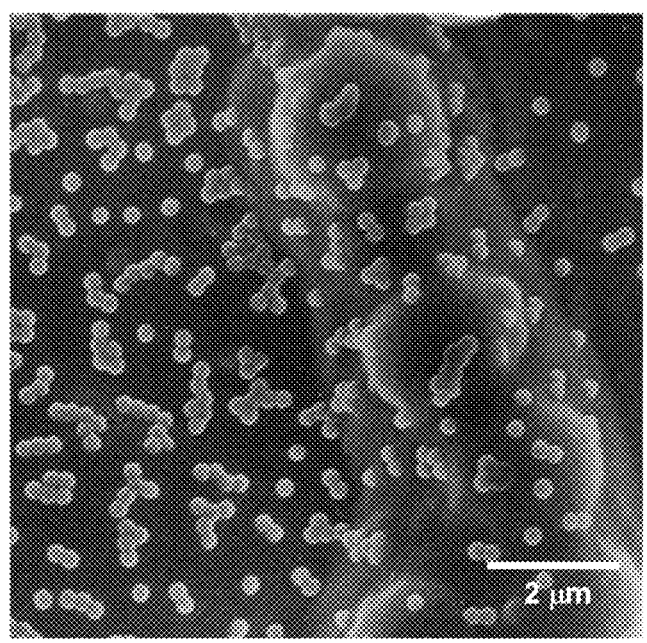
FIG. 14 shows an LbL nanosheet modified with different latex beads on its A and B surfaces as seen through a scanning electron microscope.

Next, 2 µm and 200 nm LB were bonded on the A surface and the B surface of the nanosheet, respectively, using the method in Example 3-3. Upon observation with a scanning electron microscope, it was observed that the 200 nm LB supported on the A surface are scattered across from the 2 µm LB supported on the B surface (FIG. 14). The profile of the B surface LB was expressed by the coating of the nanosheet and, since no fractured areas were visible on the A surface of the sheet, the flexibility of the nanosheet was confirmed.

EXAMPLE 3-5

Figure 15:
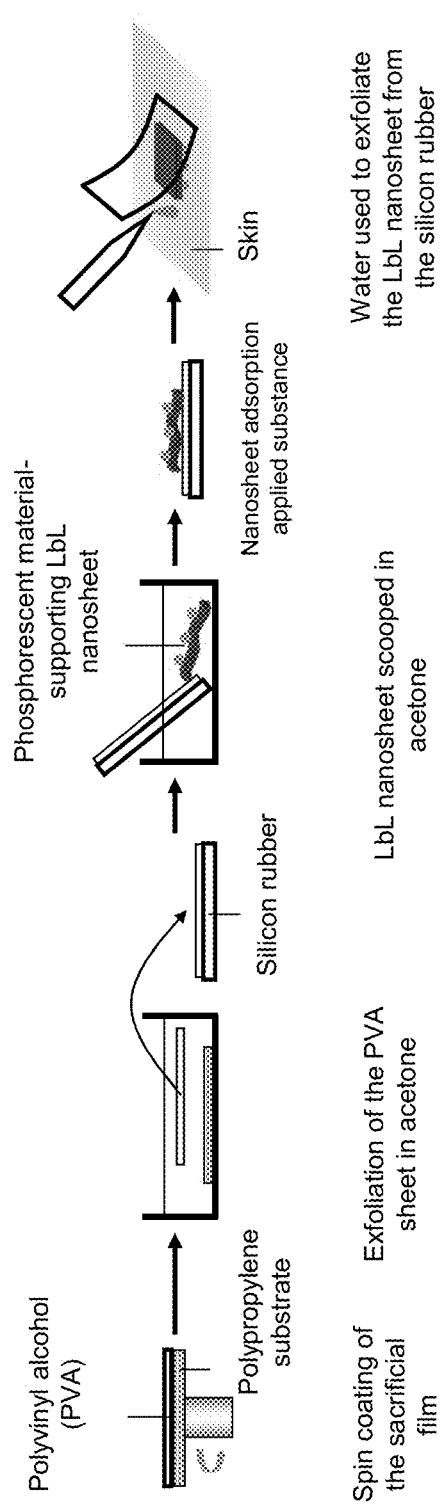
FIG. 15 shows production of a nanosheet that uses a water-soluble support film and a method for applying a nanosheet to skin.

Production of an LbL Nanosheet Using a Soluble Support Film and Adhesion of Said Film to Skin In the present example, a nanosheet was produced and adhered to the skin through the following steps (FIG. 15).
1. Polyvinyl alcohol (PVA) was spin coated (800 rpm, 3 seconds/7000 rpm, 20 seconds) on a polypropylene substrate (5 cm×5 cm) as a support film.
2. PVA was exfoliated as a sheet (size: ca 5 cm×5 cm, thickness ca 1.3 µm) from a polypropylene substrate in acetone.
3. Mounting (adsorption) of a PVA sheet on a silicon rubber substrate
4. A luminescent pigment supported LbL nanosheet was absorbed to a silicon rubber substrate with PVA mounted thereon.
5. The silicon rubber substrate in 4. above was adhered to the skin, then the silicon rubber substrate was exfoliated while dissolving the PVA sheet with water, after which the luminescent pigment supported LbL nanosheet was adhered to the skin.

Figure 16:
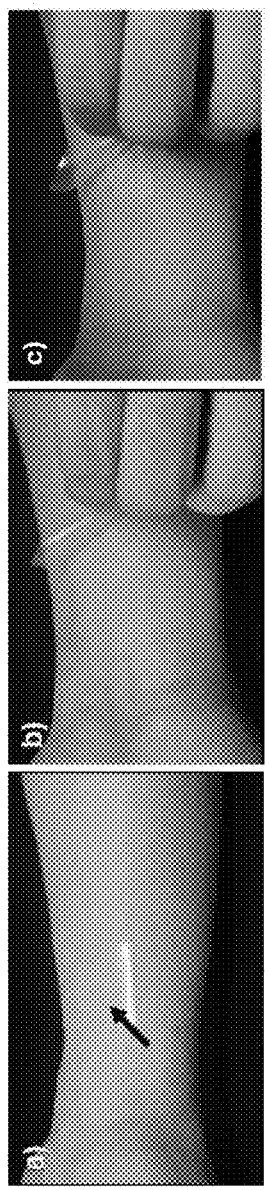
FIG. 16 shows a nanosheet adhered atop skin.

A luminescent pigment supporting LbL nanosheet was adsorbed to a PVA-silicon rubber substrate. When the PVA-silicon rubber substrate was applied to the surface of the skin, a slight reflection of the nanosheet surface made it possible to confirm the existence of a nanosheet in the shape of the PVA silicon rubber substrate (FIG. 16a arrow). The surface of the skin was moistened with a small amount of water. Also, when the PVA-silicon rubber substrate was applied in the same way as above, the PVA layer dissolved instantly and exfoliation of the silicon rubber which forms the substrate body as well as easy transfer of the LbL nanosheet onto the skin were successful. The LbL nanosheet adsorbed to the skin surface is difficult to verify under visible light (FIG. 16b). The LbL nanosheet is highly adhesive. On the other hand, when the skin site to which the sheet was attached was irradiated with a blacklight, emission of light from the luminescent pigment made it possible to observe that the LbL nanosheet maintained its shape on the silicon rubber substrate while applied to the skin surface (FIG. 16c). The above showed that a nanosheet with an aspect ratio exceeding 1,000,000 is able to apply on the skin.

EXAMPLE 4

Production of a Poly(lactide-co-glycolide) Nanoparticle Heat-fusion Nanosheet (PLGA Nanosheet) Having an Identical Functional Substance Bonded to the A Surface and B Surface Thereof

EXAMPLE 4-1

Figure 17:
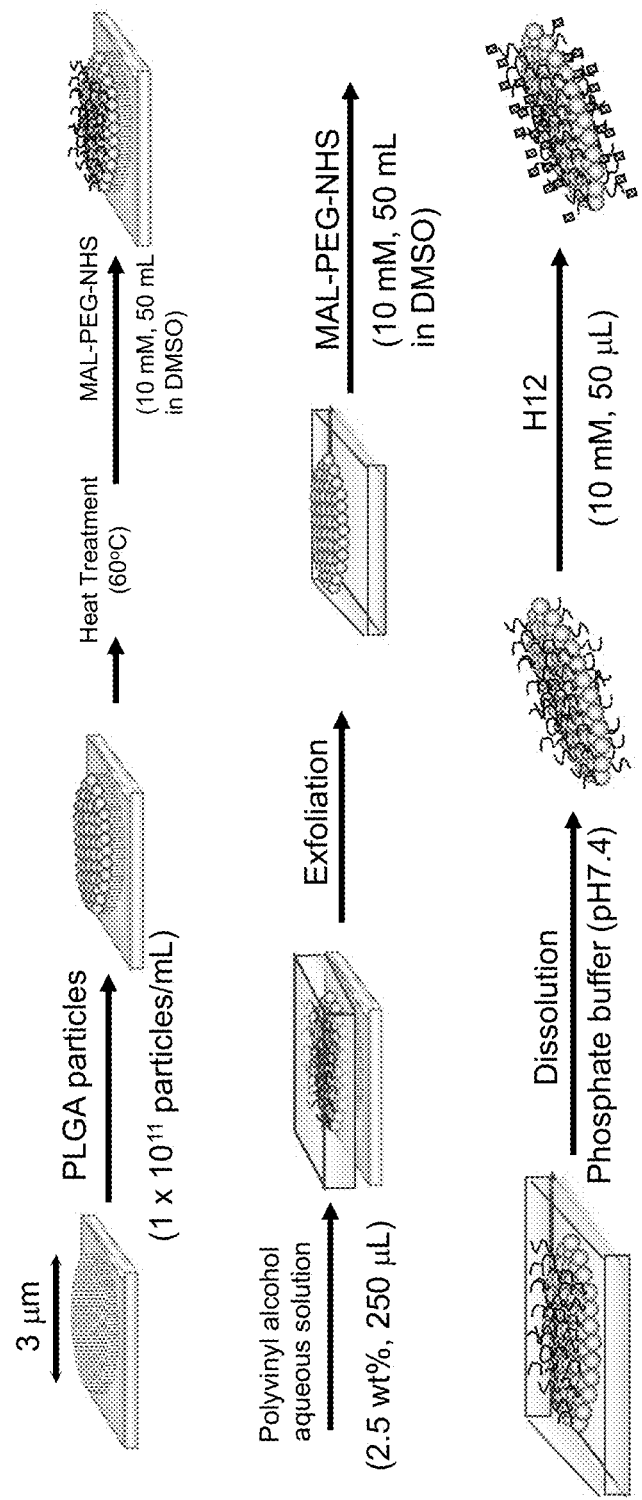
FIG. 17 shows preparation of a PLGA nanosheet that uses a disk-shaped pattern (3 μm) and a method for double-sided modification with fibrinogen-derived dodecapeptide (H12).

Preparation of a PLGA Nanosheet Using a Disk-shaped Pattern (3 µm) and Modified on Both Sides with Fibrinogen-derived Dodecapeptide (H12) (FIG. 17)

Figure 18:
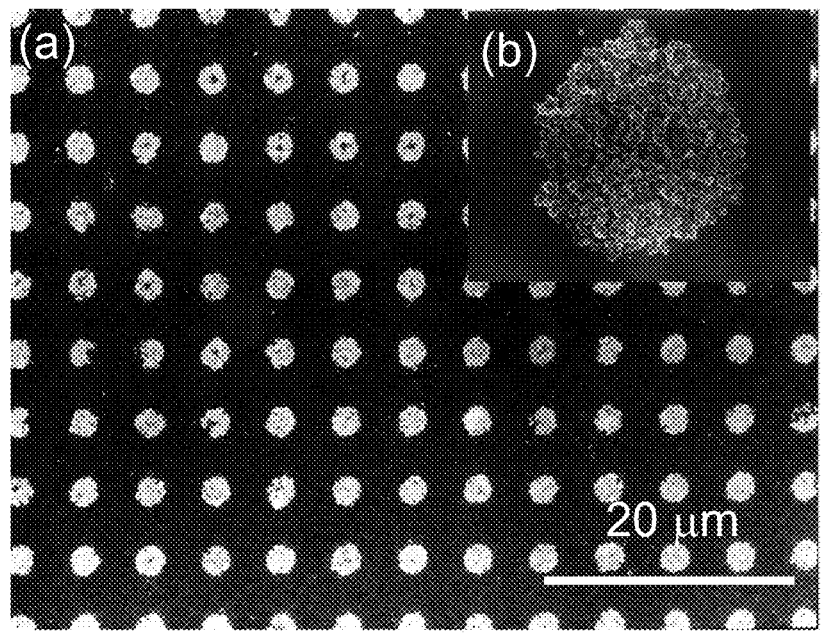
FIG. 18 shows selective adsorption of a disk-shape patterned PLGA nanosheet.

In this example, a PLGA nanosheet was formed, and both sides were modified with H12. When PLGA nanoparticle dispersion (1×10$^{11}$ particles/mL, pH 7.4) was dripped on the ODS disk-shaped pattern substrate and blown away with N$_2$ gas, the PLGA nanoparticles adhered uniformly to the entirety of the substrate. However, when the substrate was washed several times with distilled water, it was observed that the PLGA nanoparticles remained densely adhered to only the ODS region and adhered selectively (FIG. 18(a)). The adhered nanoparticles were densely arranged on a dot pattern and maintained a circular shape (FIG. 18(b)). After heat fusion (60° C., 2 minutes), a dispersed H12-PLGA nanosheet with H12 bonded to both its face and reverse face was prepared.

EXAMPLE 4-2

Interaction Between the H12-PLGA Nanosheet and the Activated Platelets

After platelets (600 μL, 6.0×10$^6$ platelets) were added to the H12-PLGA sheet (300 μL, approximately 3.0×10$^6$ sheets); platelets were activated with adenosine 5'-diphosphate (1 mM, 90 μL) and shaken (30 min, 37° C.). After fixation with glutaraldehyde (1.0%), adsorbtion to the poly(L-lysine)-fixed substrate (1 hr, r.t.) was performed, fixation with 1% (w/v) osmium tetroxide followed by alcohol dehydration was performed, and observations were conducted in the same manner as they were with a scanning electron microscope.

Figure 19:
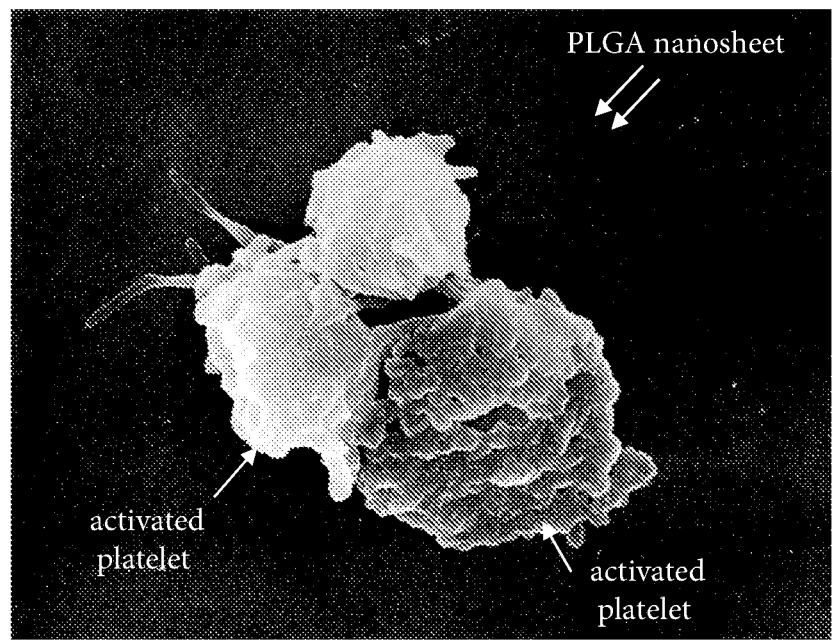
FIG. 19 is a scanning electron microscope photograph that shows interaction between a PLGA nanosheet (double arrow) and an activated platelet (single arrow).

As a result, the activated platelets specifically bonded to both faces of the sheet and the disk shape of the nanosheet was maintained (FIG. 19).

EXAMPLE 4-3

Observation of the Adhesion Behavior of H12-PLGA Nanosheet Under Flow Condition

H12-PLGA nanosheet (8.0×10$^6$ sheets) was added to blood ([PLT]=20×10$^4$/μL, 500 μL) to which anticoagulant PPACK (f.c. 40 μM) was added, blood was allowed to flow onto the collagen-fixed substrate at a low shear rate (100 s$^{-1}$), then video was filmed using a fluorescent microscope and a CCD camera.

Figure 20:
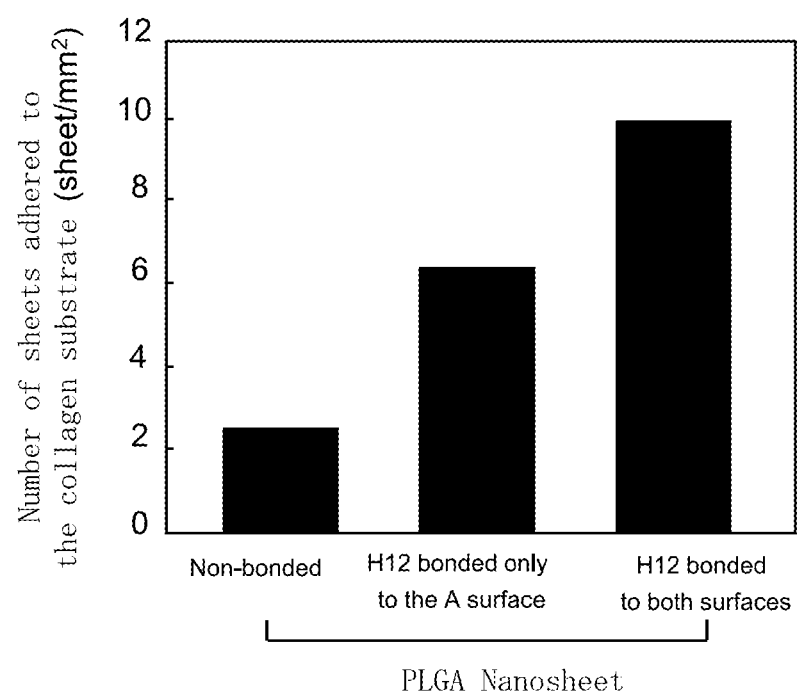
FIG. 20 shows a comparison of the number of adhesions to the collagen substrate of the H12-PLGA nanosheet (180 seconds after the start of flow).

Although the FITC-labeled H12 non-bonded PLGA nanosheet dispersion was added to the blood, after the blood was allowed to flow (shear rate 100 s$^{-1}$) onto the collagen-immobilized substrate and contacted with (rolled on) the substrate, the majority of the sheets did not adhere (FIG. 20). When a dispersion of PLGA nanosheets with H12 bonded to the A surface alone, or a dispersion of HA-PLGA nanosheets with H12 bonded to the both sides was allowed to flow in the same way, the quantity of bonded H12 increased (comparing modification of the A surface alone with modification of both sides) and an irreversibly adhering sheet increased (FIG. 20). This effect was determined to be caused by specific interaction between the H12 bonded to the sheet and the activated platelets adhered to the collagen substrate. Accordingly, to possess both the adhesive function (slows down speed) and the irreversible adhesion function with activated platelets, it is believed that it may be advantageous to modify H12 on both sides.

EXAMPLE 4-4

Evaluation of H12-PLGA Nanosheet Platelet Aggregation Promotion Ability

Figure 21:
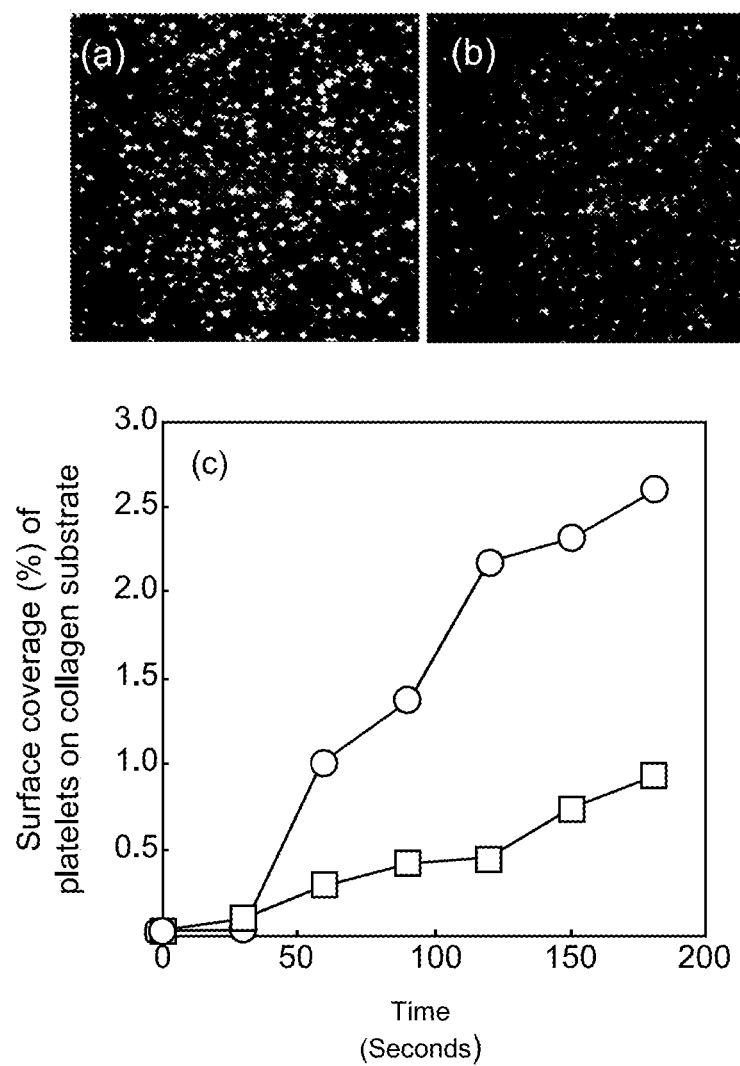
FIG. 21(a) shows an image of platelet adherence in the presence of an H12-PLGA nanosheet (180 seconds after the start of flow)
FIG. 21(b) shows platelet adherence in the absence of an H12-PLGA nanosheet (180 seconds after the start of flow)
FIG. 21(c) shows the change over time in platelet adherence in the presence (○) and absence (□) of an H12-PLGA nanosheet.

When only the platelets (f.c. 1.0×10$^4$/μL) in thrombocytopenic blood were FITC-labeled and allowed to flow (shear rate 100 s$^{-1}$) onto a collagen-immobilized substrate, platelets adhered over time, and surface coverage (SC) was 0.9% after 180 seconds (FIG. 21(b) and the "□" in FIG. 21(c)). Then, when non-fluorescent labeled H12-PLGA sheets dispersion was added, platelet SC increased precipitously after 60 seconds elapsed and SC increased approximately 300% (SC: 2.6%) after 180 seconds (FIG. 21(a), and the "○" in FIG. 21(c)). This hints that adhesion of H12-PLGA sheet was first induced by adhesion of the platelets to the substrate. It is considered that an H12-PLGA sheet adhered to the activated platelets, and that this adhesion led to induction and adhesion of flowing platelets.

Accordingly, the possibility was shown that the H12-PLGA sheet becomes a flat scaffolding, that the surface area increases, and that the H12-PLGA sheet increases the aggregation promotion ability of the flowing platelets.

EXAMPLE 5

Production of a Polylactic Acid (PLA) Nanosheet, Poly(lactic-co-glycolic acid) (PLGA) Nanosheet, and Polycaprolactone (PCL) Nanosheet Having a Huge Aspect Ratio and a Different Functional Substance on the A Surface and B Surface Thereof

EXAMPLE 5-1

Exfoliation of a PLA Nanosheeet that Uses a Soluble Support Sheet

Figure 22:
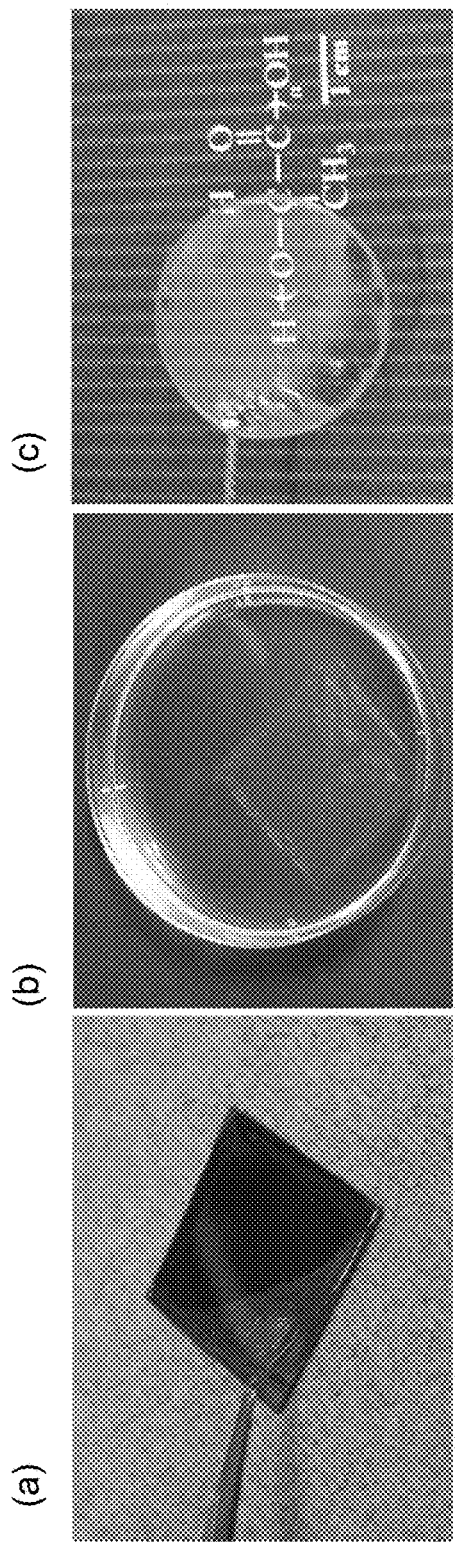
FIG. 22(a) shows exfoliation of a PLA nanosheet that uses a PVA support film from an SiO$_2$ substrate.
FIG. 22(b) shows a PLA nanosheet dispersed in an aqueous solution.
FIG. 22(c) shows a colorless, transparent PLA nanosheet scooped in a metal frame.

A PLA (weight-average molecular weight: 80,000) methylene chloride solution (5 mg/mL) was spin coated on the SiO$_2$ substrate and heated to dry (50° C., 90 seconds). Then, a stylus thickness meter was used to measure the film thickness, which was 23±5 nm. Next, when a 2 wt % polyvinyl alcohol (PVA) aqueous solution was cast and heated to dry (70° C., 15 minutes), it was possible to easily exfoliate a PVA cast film with tweezers, thereby obtaining a flexible yet strong transparent film (FIG. 22(a)). When a PVA cast film was immersed in purified water, the PVA dissolved instantly and, simultaneously, a colorless, transparent PLA nanosheet dispersion was obtained (FIG. 22(b)).

Using this method, it is possible to exfoliate PLA nanosheets of various thicknesses. In addition, PLGA nanosheet (film thickness 18±6 nm), PCL nanosheet (film thickness 18±5 nm) dispersions were obtained. Also, the PLA nanosheet dispersion can be scooped with a metal frame and extracted in atmosphere. The sheet did not fracture even when dried (FIG. 22(c)).

EXAMPLE 5-2

Formation of a PLA Nanosheet Having a Different Functional Substance on the A Surface and B Surface Thereof A 20 mg/mL PVA aqueous solution was spin coated on a SiO$_2$ substrate and dried by heating (70° C., 15 minutes). Next, a 5 mg/mL PLA dichloromethane solution was spin coated and dried by heating (70° C., 15 minutes) to produce a PLA nanosheet.

Figure 23:
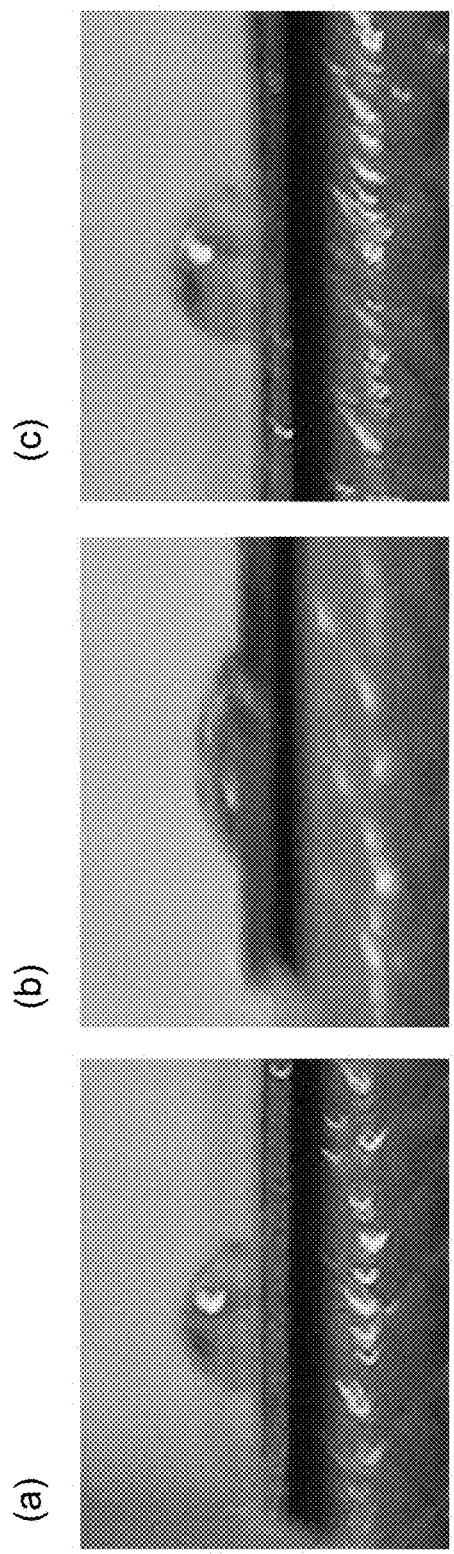
FIG. 23 shows contact angle measurements for a PLA nanosheet on which rHSA is adsorbed only on the A surface.

The contact angle of the A surface of the PLA nanosheet SiO$_2$ substrate was 74 ±5° (FIG. 23(a), Table 1). The A surface of the PLA nanosheet atop SiO$_2$ substrate was coated with a recombinant human serum albumin (rHSA) aqueous solution (50 mg/mL) and left stationary for 1 hour at room temperature. The A surface of the substrate was then washed with pure water. After drying, the contact angle was significantly decreased to 21±30 (FIG. 23(b), Table 1). The decrease of the contact angle was considered to be the result of rHSA modification of the A surface of the substrate.

Next, when this substrate was immersed in pure water, the PVA sacrificial film dissolved, and the PLA nanosheet was exfoliated. This PLA nanosheet was applied to the substrate so that the B surface of said nanosheet would face up, after which the SiO$_2$ substrate was cleaned with pure water and then dried. This contact angle was 78±6° (FIG. 23(c), Table 1), almost identical to that of the A surface prior to rHSA adsorption. It was considered that rHSA did not exist on the B surface. Accordingly, a PLA nanosheet having a different functional substance on the A surface and B surface thereof was successfully formed.

TABLE 1

Contact angle measurement of the PLA nanosheet with rHSA adsorption at the A surface only

|  |  | Contact angle (°) |
|---|---|---|
| PLA nanosheet A surface | Before rHSA adsorption | 74 ± 5 |
|  | After rHSA adsorption | 21 ± 3 |
| PLA nanosheet B surface |  | 78 ± 6 |

EXAMPLE 6

The present example shows an LbL nanosheet applied to a rat cecum.

In the method explained in (1) to (5) below, an LbL nanosheet was directly formed on an SiO$_2$ substrate.
(1) Spin-coating was performed (4500 rpm, 15 seconds) using a chitosan aqueous solution ($M_w$: 88 kDa, 1 mg/mL, 1% acetic acid/0.5M NaCl).
(2) The substrate surface was spin coated and washed with distilled water two times.
(3) Spin-coating was performed (4500 rpm, 15 seconds) using sodium alginate ($M_w$: 106 kDa, 1 mg/mL, 0.5M NaCl).
(4) The substrate surface was spin coated and washed with distilled water twice.
(5) Hereinbelow, steps (1) to (4) are repeated to produce an LbL nanosheet-fixed substrate comprising 21 layers.

Next, a 10 wt % polyvinyl alcohol (PVA) aqueous solution was cast onto an LbL nanosheet —SiO$_2$ substrate supporting a small amount of luminescent pigment. After the substrate was dried in a dessicator (room temperature, 12 hours), the PVA cast film onto which the LbL nanosheet was transferred was successfully exfoliated from the substrate.

Figure 24:
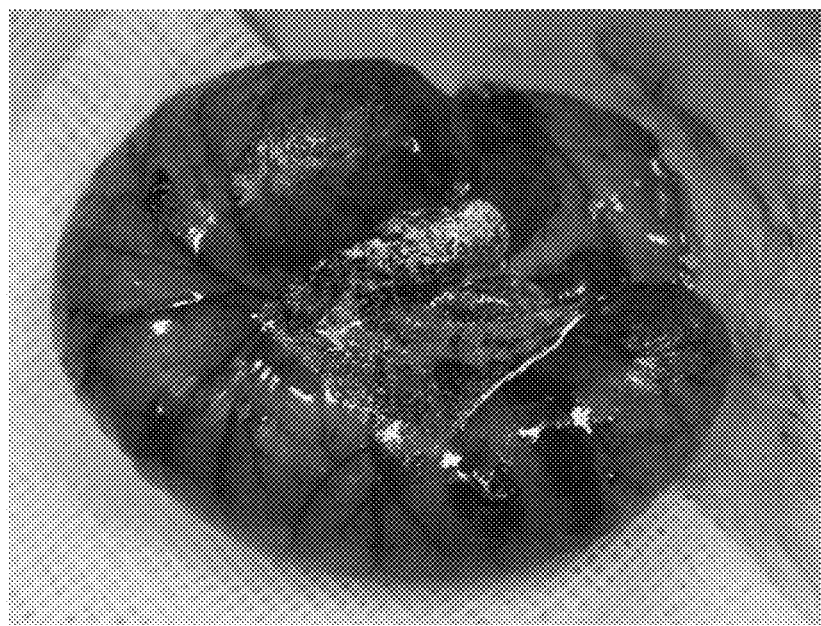
FIG. 24 shows a rat cecum to which an LbL nanosheet supporting a small amount of luminescent pigment has been applied as viewed under a blacklight.

Then, the LbL nanosheet having PVA film was applied so that the rat cecum contacted the LbL nanosheet side. When the PVA was dissolved in normal saline solution, only the LbL nanosheet remained (observed under a blacklight), and the LbL nanosheet could be tightly applied in the shape of the cecum (FIG. 24).

INDUSTRIAL APPLICABILITY

The present invention provides a thin film polymer structure having identical or different functional substances on its face and reverse face. The structure of the present invention can be used as a functional carrier or a platelet substitute in a drug delivery system, a wound coating material, a coagulation inhibitor, or a topical skin product such as a skin care product.

The invention claimed is:

1. A method for preparing a thin film polymer structure, wherein the thin film polymer structure prepared by the method has two faces, one face being each of the opposite sides of the thin film polymer structure, and has a different functional substance bound to each of the two faces, said thin film polymer structure being obtained by the steps of:
   (a) adsorbing polyfunctional molecules to an arbitrarily shaped soluble region of a substrate body in an interface between the substrate body and a liquid phase, wherein the polyfunctional molecules are at least one polyfunctional macromer selected from the group consisting of polylactic acid, polylactic acid/glycolic acid copolymer, and polycaprolactone, provided that said polyfunctional macromer is not a polymer bead;
   (b) crosslinking the adsorbing polyfunctional molecules by thermally crosslinking the polyfunctional molecules at 60-120° C. to form a polymer thin film having two faces, an exposed face referred to as an A surface and a reverse face on the opposite side of the thin film facing the substrate body, the reverse face referred to as a B surface;
   (c) bonding a functional substance to the A surface of the formed polymer thin film;
   (d) exfoliating the polymer thin film from the substrate body by dissolving the soluble region of the substrate body with a solvent;
   (e) applying the A surface inclusive of the bonded functional substance of the exfoliated polymer thin film directly atop a soluble support film formed on a substrate body other than the substrate body in step (a) the soluble support film being formed by application of an aqueous solution comprising a soluble support film polymer to the substrate body other than the substrate body in step (a), wherein said A surface inclusive of the bonded functional substance of the exfoliated polymer thin film bonds to the soluble support film solely by secondary bonding forces between the A surface inclusive of the bonded functional substance of the exfoliated polymer thin film and the soluble support film;
   (f) bonding to the B surface of the polymer thin film a functional substance different from the functional substance in step (c); and
   (g) dissolving the soluble support film with a solvent to release a thin film polymer structure having a different functional substance on the A surface and the B surface of the thin film polymer structure,
   wherein each of the soluble support film and soluble region is independently formed of polyethylene glycol, polyacrylamide, polyvinyl alcohol, or polysaccharide, said polysaccharide excluding cellulose acetate.

2. The method according to claim 1, wherein the functional substance is at least one of the following selected from the group consisting of a polymer compound, a polyelectrolyte, a protein, a peptide, a polysaccharide and a biotin derivative.

3. The method according to claim 2, wherein the polymer compound comprises poly(ethyleneglycol).

4. The method according to claim 1, wherein the substrate bodies are entirely or partially formed of at least one of the following selected from the group consisting of a metal or an oxide cover layer thereof, silicon, silicon rubber, silica, glass, mica, graphite, an organic polymer, and apatite.

5. The method according to claim 1, wherein the solvent in steps (d) and (g) is selected from acetone, ethyl acetate, an alcohol, water, or an aqueous solution and will not dissolve the thin film polymer structure.

6. The method according to claim 1, wherein the A surface of the exfoliated polymer thin film bonds to the soluble support film by a secondary bonding force selected from the group consisting of electrostatic interaction, hydrogen bonding or Van der Waals' force.

7. A method for preparing a thin film polymer structure, wherein the thin film polymer structure prepared by the method has two faces, one face being each of the opposite sides of the thin film polymer structure, and has a different functional substance bound to each of the two faces, said thin film polymer structure being obtained by the steps of:
(a) adsorbing polyfunctional molecules to an arbitrarily shaped soluble region of a substrate body in an interface between the substrate body and a liquid phase, wherein the polyfunctional molecules are at least one polyfunctional macromer selected from the group consisting of polylactic acid, polylactic acid/glycolic acid copolymer, and polycaprolactone, provided that said polyfunctional macromer is not a polymer bead;
(b) crosslinking the adsorbing polyfunctional molecules by thermally crosslinking the polyfunctional molecules at 60-120° C. to form a polymer thin film having two faces, an exposed face referred to as an A surface and a reverse face on the opposite side of the thin film facing the substrate body, the reverse face referred to as a B surface;
(c) bonding a functional substance to the A surface of the formed polymer thin film;
(d) exfoliating the polymer thin film from the substrate body by dissolving the soluble region of the substrate body with a first solvent;
(e) applying the A surface inclusive of the bonded functional substance of the exfoliated polymer thin film directly atop a soluble support film formed on a substrate body other than the substrate body in step (a), wherein said A surface inclusive of the bonded functional substance of the exfoliated polymer thin film bonds to the soluble support film solely by secondary bonding forces between the A surface inclusive of the bonded functional substance of the exfoliated polymer thin film and the soluble support film;
(f) bonding to the B surface of the polymer thin film a functional substance different from the functional substance in step (c); and
(g) dissolving the soluble support film with a solution consisting essentially of a second solvent selected from the group consisting of acetone, ethyl acetate, an alcohol, water, and a mixture thereof to release a thin film polymer structure having a different functional substance on the A surface and the B surface of the thin film polymer structure,
wherein each of the soluble support film and soluble region is independently formed of polyethylene glycol, polyacrylamide, polyvinyl alcohol, or polysaccharide, said polysaccharide excluding cellulose acetate.

8. The method according to claim 7, wherein the second solvent is water.

* * * * *